US009290759B2

(12) United States Patent
Abeliovich et al.

(10) Patent No.: US 9,290,759 B2
(45) Date of Patent: Mar. 22, 2016

(54) OPTIMIZED MIRNA CONSTRUCTS

(75) Inventors: Asa Abeliovich, New York, NY (US);
Hervé Rhinn, New York, NY (US);
Toru Yamashita, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 86 days.

(21) Appl. No.: 13/818,956

(22) PCT Filed: Aug. 25, 2011

(86) PCT No.: PCT/US2011/049126
§ 371 (c)(1),
(2), (4) Date: Oct. 28, 2013

(87) PCT Pub. No.: WO2012/027558
PCT Pub. Date: Mar. 1, 2012

(65) Prior Publication Data
US 2014/0051748 A1   Feb. 20, 2014

Related U.S. Application Data

(60) Provisional application No. 61/376,922, filed on Aug. 25, 2010.

(51) Int. Cl.
*C07H 21/02*   (2006.01)
*C12N 15/11*   (2006.01)
*C12N 15/113*  (2010.01)

(52) U.S. Cl.
CPC ............ *C12N 15/113* (2013.01); *C12N 15/111* (2013.01); *C12N 2310/141* (2013.01); *C12N 2330/00* (2013.01)

(58) Field of Classification Search
None
See application file for complete search history.

(56) References Cited

U.S. PATENT DOCUMENTS

| | | | | |
|---|---|---|---|---|
| 5,863,902 A * | 1/1999 | Munoz | .................. | C07C 237/22 514/17.7 |
| 6,451,343 B1 * | 9/2002 | Glinecke | .............. | A61K 9/2009 424/464 |
| 8,183,219 B2 * | 5/2012 | Burright | .............. | C07K 14/475 514/44 A |
| 8,454,954 B2 * | 6/2013 | Schlossmacher | ...... | A61K 31/00 424/130.1 |
| 2007/0026403 A1 | 2/2007 | Hatzigeorgiou et al. | | |
| 2008/0313773 A1 | 12/2008 | Chua et al. | | |
| 2009/0082298 A1* | 3/2009 | Dickins et al. | .................. | 514/44 |
| 2010/0040601 A1 | 2/2010 | Cantin et al. | | |

FOREIGN PATENT DOCUMENTS

WO   WO-2008033285 A2   3/2008

OTHER PUBLICATIONS http://www.mirbase.org/cgi-bin/mirna_entry.pl?acc=MI0000437, retrieved from the web on Feb. 25, 2015.*
Goljanek-Whysall (Journal of Cell Science 125 (15): 3590-3600, 2012), including supplementary material.*
Lu PY, Woodle MC.: "Delivering small interfering RNA for novel therapeutics" Methods Mol Biol. 2008;437:93-107.
Saghir Akhtar and Ibrahim F. Benter: "Nonviral delivery of synthetic siRNAs in vivo" *J. Clin. Invest.* 117(12): 3623-3632 (2007).
Huricha Baigude, Dr., Tariq M. Rana "Delivery of Therapeutic RNAi by Nanovehicles", *ChemBioChem* .vol. 10 Issue 15, pp. 2449-2454. Oct. 12, 2009.
Keller M.. "Nanomedicinal delivery approaches for therapeutic siRNA." Int J Pharm. Sep. 11, 2009;379(2):210-211.
Meade BR, Dowdy SF. "The road to therapeutic RNA interference (RNAi): Tackling the 800 pound siRNA delivery gorilla." Discov Med. Dec. 2009;8(43):253-256.
Akin Akinc et al. "Development of Lipidoid-siRNA Formulations for Systemic Delivery to the Liver", *Molecular Therapy* (2009) 17 5, 872-879.
William M. Pardridge "shRNA and siRNA delivery to the brain" *Advanced Drug Delivery Reviews*, vol. 59, Issues 2-3, Mar. 30, 2007, pp. 141-152.
Saroj P Mathupala, "Delivery of small-interfering RNA (siRNA) to the brain" *Expert Opinion on Therapeutic Patents*, Feb. 2009, vol. 19, No. 2, pp. 137-140.
Gillardon et al., "MicroRNA and proteome expression profiling in early-symptomatic α-synuclein(A30P)-transgenic mice", Proteomics Clin. Appl., 2008, vol. 2, pp. 697-705.
Abeliovich, A., et al. Mice lacking alpha-synuclein display functional deficits in the nigrostriatal dopamine system. *Neuron* 25, 239-252 (2000).
Dauer, W., et al. Resistance of alpha-synuclein null mice to the parkinsonian neurotoxin MPTP. *Proc Natl Acad Sci U S A* 99, 14524-14529 (2002).
Klivenyi, P., et al. Mice lacking alpha-synuclein are resistant to mitochondrial toxins. *Neurobiol Dis* 21, 541-548 (2006).
Gorbatyuk, O.S., et al. In Vivo RNAi-Mediated alpha-Synuclein Silencing Induces Nigrostriatal Degeneration. *Mol Ther*., Aug. 2010, vol. 18, No. 8, pp. 1450-1457.
Bartel, D.P. MicroRNAs: genomics, biogenesis, mechanism, and function. *Cell* 116, 281-297 (2004).
Saba, R. & Schratt, G.M. MicroRNAs in neuronal development, function and dysfunction. *Brain Res* 1338, 3-13. Apr. 2010.
Davidson, B.L. & Boudreau, R.L. RNA interference: a tool for querying nervous system function and an emerging therapy. *Neuron* 53, 781-788 (2007).
Su, H., Trombly, M.I., Chen, J. & Wang, X. Essential and overlapping functions for mammalian Argonautes in microRNA silencing. *Genes Dev* 23, 304-317 (2009).
Grimm, D., et al. Fatality in mice due to oversaturation of cellular microRNA/short hairpin RNA pathways. *Nature* 441, 537-541 (2006).

(Continued)

*Primary Examiner* — Richard Schnizer
(74) *Attorney, Agent, or Firm* — Wilmer Cutler Pickering Hale and Dorr LLP

(57) ABSTRACT

The invention provides optimized miRNA sequences and their therapeutic use. The invention provides optimized miRNA constructs for treatment of neurodegenerative diseases.

8 Claims, 11 Drawing Sheets

(56) References Cited

OTHER PUBLICATIONS

McBride, J.L., et al. Artificial miRNAs mitigate shRNA-mediated toxicity in the brain: implications for the therapeutic development of RNAi. *Proc Natl Acad Sci U S A* 105, 5868-5873 (2008).
Lewis, J., et al. In vivo silencing of alpha-synuclein using naked siRNA. *Mol Neurodegener*, 2008, vol. 3, No. 19, pp. 1-10.
Kumar, P., et al. Transvascular delivery of small interfering RNA to the central nervous system. *Nature* 448, 39-43 (2007).
Nguyen, T., Menocal, E.M., Harborth, J. & Fruehauf, J.H. RNAi therapeutics: an update on delivery. *Curr Opin Mol Ther* 10, 158-167 (2008).
Doxakis, E. Post-transcriptional regulation of alpha-synuclein expression by mir-7 and mir-153. *J Biol Chem* 285, Jan. 27, 2010, 1-14.
Junn, E., et al. Repression of alpha-synuclein expression and toxicity by microRNA-7. *Proc Natl Acad Sci U S A* 106, 13052-13057 (2009).
Gondai, T., et al., Short-hairpin RNAs synthesized by T7 phage polymerase do not induce interferon. *Nucleic Acids Res*, Jan. 21, 2008, vol. 36, No. 3, 8 pages.
Kuo, Y.M., et al. Extensive enteric nervous system abnormalities in mice transgenic for artificial chromosomes containing Parkinson disease-associated alpha-synuclein gene mutations precede central nervous system changes. *Hum Mol Genet* 19, 1633-1650. Jan. 27, 2010.
Thakker, D.R., et al. Neurochemical and behavioral consequences of widespread gene knockdown in the adult mouse brain by using nonviral RNA interference. *Proc Natl Acad Sci U S A* 101, 17270-17275 (2004).
Thakker, D.R., et al. siRNA-mediated knockdown of the serotonin transporter in the adult mouse brain. *Mol Psychiatry* 10, 782-789, (2005).
Yamashita, T., et al. Dissociation and protection of the neurovascular unit after thrombolysis and reperfusion in ischemic rat brain. *J Cereb Blood Flow Metab* 29, 715-725 (2009).
Macleod, D., et al. The Familial Parkinsonism Gene LRRK2 Regulates Neurite Process Morphology. *Neuron* 52, 587-593 (2006).
Pulford, B., et al. Liposome-siRNA-peptide complexes cross the blood-brain barrier and significantly decrease PrP on neuronal cells and PrP in infected cell cultures. *PLoS One* 5, Jun. 2010, vol. 5, No. 6, 13 pages.
Conaco, C., et al., Reciprocal actions of REST and a microRNA promote neuronal identity. Proc Natl Acad Sci U S A, 2006. 103(7): p. 2422-2427.
Gispert, S., et al., Transgenic mice expressing mutant A53T human aSyn show neuronal dysfunction in the absence of aggregate formation. Mol Cell Neurosci. 2003 24(2):p. 419-429.
Griffiths-Jones, S., et al., miRBase: microRNA sequences, targets and gene nomenclature. Nucleic Acids Res, 2006. 34(Database issue): p. D140-D144.
Gründemann, J., et al., Elevated aSyn mRNA levels in individual UV-laser-microdissected dopaminergic substantia nigra neurons in idiopathic Parkinson's disease Nucleic Acids Res. 2008 36(7), 16 pages.

Hayashita-Kinoh, H., et al., Down-regulation of aSyn expression can rescue dopaminergic cells from cell death in the substantia nigra of Parkinson's disease rat model. Biochem Biophys Res Commun. 2006 341(4):p. 1088-1095.
He, L. and G.J. Hannon, MicroRNAs: small RNAs with a big role in gene regulation. Nat Rev Genet, 2004. 5(7): p. 522-531.
He L., et al., A microRNA polycistron as a potential human oncogene. Nature. 2005 435(7043): p. 828-833.
John, B., et al., Human MicroRNA targets. PLoS Biol, 2004. 2(11): pp. 1862-1879.
Johnston, R.J., Jr., et al., MicroRNAs acting in a double-negative feedback loop to control a neuronal cell fate decision. Proc Natl Acad Sci U S A, 2005. 102(35): p. 12449-12454.
Kawasaki, H. and K. Taira, Hes1 is a target of microRNA-23 during retinoic-acid-induced neuronal differentiation of NT2 cells. Nature, 2003. 423(6942): p. 838-842.
Kim, J., et al., A MicroRNA feedback circuit in midbrain dopamine neurons. Science, 2007. 317(5842): p. 1220-1224.
Kirk, D. and Bjorklund, A., Modeling CNS neurodegeneration by overexpression of disease-causing proteins using viral vectors, Trends Neurosci. 26 (2003): p. 386-392.
Kirk, D., et al., Parkinson-Like Neurodegeneration Induced by Targeted Overexpression of Alpha-Synuclein in the Nigrostriatal System J Neurosci. 2002, 22(7):p. 2780-2791.
Krichevsky, A.M., et al., Specific microRNAs modulate embryonic stem cell-derived neurogenesis. Stem Cells, 2006. 24(4): p. 857-864.
Lewis, B.P., et al., Prediction of mammalian microRNA targets. Cell, 2003. 115(7): p. 787-798.
Martinat, C., et al., (2006). Cooperative transcription activation by Nurr1 and Pitx3 induces embryonic stem cell maturation to the midbrain dopamine neuron phenotype. Proc Natl Acad Sci U S A, 103(8):p. 2874-2879.
Sapru, MK., et al., Silencing of human aSyn in vitro and in rat brain using lentiviral-mediated RNAi. Exp Neurol. 2006 198(2):p. 382-390.
Schratt, G.M., et al., A brain-specific microRNA regulates dendritic spine development. Nature, 2006. 439(7074): p. 283-289.
Shendelman, S., et al., DJ-1 is a redox-dependent molecular chaperone that inhibits alpha-synuclein aggregate formation. PLoS Biol., Nov. 2004, vol. 2, No. 11, pp. 1764-1773.
Singleton, A.B., et al., ASyn locus triplication causes Parkinson's disease. Science, 2003. 302(5646): p. 841.
Spillantini, M.G., et al., ASyn in Lewy bodies. Nature, 1997. 388(6645): pp. 839-840.
Vo, N., et al., A cAMP-response element binding protein-induced microRNA regulates neuronal morphogenesis. Proc Natl Acad Sci U S A, 2005. 102(45): pp. 16426-16431.
International Search Report and Written Opinion issued by the United States Patent and Trademark Office as International Searching Authority for International Application No. PCT/US11/49126 mailed Mar. 9, 2012 (13 pages).

\* cited by examiner

OPTIMIZED MIRNA CONSTRUCTS

This application claims the benefit of priority of International Application No.: PCT/US2011/049126 filed Aug. 25, 2011, which claims the benefit of priority of U.S. Ser. No. 61/376,922 filed Aug. 25, 2010, the contents of which are hereby incorporated by reference in their entirety.

The contents of all patent and non-patent references and publications referenced throughout the specification are hereby incorporated by reference in their entirety.

The instant application contains a Sequence Listing which has been submitted in ASCII format via EFS-Web and is hereby incorporated by reference in its entirety. Said ASCII copy, created on Aug. 25, 2011, is named 19240907.txt and is 37,601 bytes in size.

FIELD OF THE INVENTION

The invention is directed to RNAi therapeutic agents based on optimized miRNAs, methods of optimizing miRNAs and methods of using such optimized miRNAs.

BACKGROUND OF THE INVENTION

RNA interference or silencing refers to the process of sequence-specific post-transcriptional gene regulation in eukaryotes which is mediated by small RNAs. Small RNA molecules have emerged as critical regulators of gene expression and function in eukaryotic genomes.

SUMMARY OF THE INVENTION

In certain aspects, the invention provides a modified pre-miR-XXX (pre-smiR-XXX), which in non-limiting embodiments is capable of forming a pre-miRNA-like miRNA/miRNA* stem-loop structure, comprising, consisting essentially of, or consisting of the following nucleic acid sequences in the 5' to 3' direction: [Gn]-[Nm] which comprises [smiRNA-XXX]-[Ns] which is the loop sequence of a corresponding endogenous pre-miR-XXX-[N*r] which comprises [smiRNA*-XXX]-UU, wherein n=0-5, s, m and r are determined by the sequences in the endogenous pre-miR-XXX stem-loop, and wherein the smiRNA-XXX sequence of the stem-loop is fully complementary beyond the endogenous seed sequence to a first target sequence of the corresponding endogenous miR-XXX. In certain embodiments the last two UU nucleotides are not present.

In certain aspects, the invention provides a modified pre-miR-XXX (pre-smiR-XXX), which in non-limiting embodiments is capable of forming a pre-miRNA-like miRNA/miRNA* stem-loop structure, comprising, consisting essentially of, or consisting of the following nucleic acid sequences in the 5' to 3' direction: [Gn]-[N*r] which comprises [smiRNA*-XXX]-[Ns], which is the loop sequence of a corresponding endogenous pre-miR-XXX-[Nm] which comprises [smiRNA-XXX]-UU, wherein n=0-5, s, m and r are determined by the sequences in the endogenous pre-miR-XXX, and wherein the smiR-XXX sequence of the stem-loop is fully complementary beyond the endogenous seed sequence to a first target sequence of the corresponding endogenous miR-XXX. In certain embodiments the last two UU nucleotides are not present In certain aspects, the invention provides a modified pre-miR-XXX (pre-smiR-XXX), which in non-limiting embodiments is capable of forming a pre-miRNA-like miRNA/miRNA* stem-loop structure, comprising, consisting essentially of, or consisting of the following nucleic acid sequences in the 5' to 3' direction: [Gn]-[Nm] which comprises [miR-XXX-5p]-[Ns] which is the loop sequence of a corresponding endogenous pre-miR-XXX-[Nr] which comprises [miR-XXX-3p]-UU, wherein n=0-5, s, m and r are determined by the sequences in the endogenous pre-miR-XXX stem-loop, and wherein the smiR-XXX-5p or smiRXXX-3p sequence of the stem-loop is fully complementary beyond the endogenous seed sequence to a first target sequence of the corresponding endogenous mir-XXX. In certain embodiments the last two UU nucleotides are not present In certain aspects, the invention provides a pre-smiRNA sequence which is an engineered sequence. In certain aspects, the invention provides a pre-smiRNA sequence which is synthetic. In certain aspects, the invention provides a pre-smiRNA sequence which is optimized. In certain aspects, the invention provides a pre-smiRNA sequence which is isolated. In certain aspects, the invention provides a pre-smiRNA sequence which is recombinant. In certain aspects, the invention provides a pre-smiRNA sequence which is based on a mammalian pre-miRNA. In certain aspects, the invention provides a pre-smiRNA sequence which is based on human pre-miRNA. In certain aspects, the invention provides a pre-smiRNA sequence which targets a human gene. In certain aspects, the pre-smiRNA sequences of the invention are modified endogenous pre-miRNA sequences as described herein.

In certain aspects, the invention provides a pre-smiRNA sequence, wherein the smiRNA-XXX sequence of the stem-loop is fully complementary beyond the seed sequence to a first target sequence of the corresponding endogenous miR-XXX and wherein the smiR-XXX binds the first target site to downregulate a first mRNA, which comprises the first target sequence, or its corresponding protein product.

In certain aspects, the invention provides a pre-smiRNA sequence, wherein n=0-3, n=0-5, n=0-10, n=0, 1, 2, 3, 4, 5, 6, 7, 8, 9, 10; m, r=20-35; m, r=25-35; m, r=20-33; m, r=28-35; m, r=28-33; m, r=20, 21, 22, 23, 24, 25, 26, 27, 28, 29, 30, 31, 32, 33, 34, 35; s=20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65. In certain aspects, the invention provides a pre-smiRNA sequence, wherein the length of the pre-smiRNA-XXX is determined by the length of a corresponding endogenous pre-miRNA-XXX. In certain aspects, the invention provides a pre-smiRNA sequence, wherein the length of the pre-smiRNA is 60-130 nucleotides long.

In certain aspects, the invention provides a pre-smiRNA sequence, wherein the pre-smiR-XXX is in a stem-loop structure. In certain aspects, the invention provides a pre-smiRNA sequence wherein smiRNA*-XXX is fully complementary to smiRNA-XXX sequence and no bulges are present in the smiRNA-XXX/smiRNA*-XXX stem of the stem-loop structure, referred to as ds perfected.

In certain aspects, the invention provides a pre-smiRNA sequence, wherein smiRNA*-XXX is complementary to smiRNA-XXX sequence except that there are bulges present in the smiRNA-XXX/smiRNA*-XXX stem of the stem-loop structure, wherein the bulges are at the position of the bulges in the endogenous miRNA-XXX/miRNA*-XXX stem-loop structure, referred to as ss perfected.

In certain aspects, the invention provides a pre-smiRNA sequence, wherein the sequence of the consecutive Nm nucleotides which are outside of smiR-XXX sequence is the same as the consecutive nucleotide sequence in a corresponding endogenous pre-miRNA-XXX. In certain aspects, the invention provides a pre-smiRNA sequence, wherein the sequence of the consecutive Nr nucleotides which are outside of smiR*-XXX sequence is the same as the consecutive nucleotide sequence in a corresponding endogenous pre-miRNA-XXX.

In certain aspects, the invention provides a pre-smiRNA sequence, wherein the pre-smiR-XXX is based on a human pre-miR-XXX, or wherein the pre-smiR-XXX targets human gene of interest.

In certain aspects, the invention provides a pre-smiRNA sequence, wherein the pre-smiR-XXX is conjugated to a delivery vehicle. A non-limiting example of a delivery vehicle is a peptide which is linked to the pre-smiRNA sequence by a peptide linkage. The link between the delivery vehicle and the pre-smiRNA sequence may be any suitable link which does not affect the pre-smiRNA sequence, structure or function. In certain aspects, the invention provides a pre-smiRNA sequence, wherein the pre-smiR-XXX is conjugated via peptide linkage, for example but not limited to a peptide RVG-9R ("9R" disclosed as SEQ ID NO: 92).

In certain aspects, the invention provides a pre-smiRNA sequence, wherein the pre-smiRNA is based on the endogenous pre-miR-153-1 or pre-miR-153-2 and wherein the modified pre-smiR-153-1 or pre-smiR-153-2 targets a gene associated with neurodegeneration. In certain aspects, the invention provides a pre-smiRNA sequence, wherein the pre-smiRNA is based on the endogenous pre-miR-153-1 or pre-miR-153-2 and wherein the modified pre-smiR-153-1 or pre-smiR-153-2 targets APP or alpha synuclein.

In certain aspects, the invention provides a nucleic acid sequence encoding the pre-smiRNA of the invention.

In certain aspects, the invention provides a pre-smiRNA sequence of SEQ ID NO: 6, 8, 12, 14, 16, 18, 24, 26, 33, 34, 40, 42, 48, or 50.

In certain aspects, the invention provides a composition comprising, consisting essentially of, or consisting of one or more of the pre-smiR-XXX of the invention. In certain aspects, the invention provides a composition for intracerebral delivery comprising one or more the pre-smiR-XXX the invention. In certain aspects, the invention provides a composition for intracerebral delivery comprising, consisting essentially of, or consisting of the pre-smiR-XXX of SEQ ID NOs: 6, 8, 12, 14, 16, 18, 24, 26, 33, 34, 40, 42, 48, or 50, or any combination thereof. In certain embodiments, the composition is formulated for intracerebral delivery, for example by injection. In certain embodiments, the composition is therapeutic. In certain embodiments, the compositions of the invention are effective to substantially silence expression of a gene or allele of interest thereby providing a therapeutic effect. In certain embodiments, the composition for intracerebral delivery comprises peptide linked smiRNAs, including but not limited as described herein, which affords neuronal targeting or transmembrane transduction.

In certain aspects, the invention provides a vector comprising a nucleic acid encoding one or more the pre-smiR-XXX of the invention.

In certain aspects, the invention provides various methods of using the inventive modified miRNAs. In certain embodiments, the inventive methods comprise, consist essentially of, or consist of the recited steps. In certain aspects, the invention provides a method to reduce aSyn levels in a subject in need thereof comprising administering to a subject in need thereof a therapeutic amount of pre-smiR-7-2(SNCA) (SEQ ID NO:40, or 42), pre-smiR-153-1 (SNCA) (SEQ ID NO: 6, or 8), pre-smiR-495(SNCA) (SEQ ID NO:48, or 50), or any combination thereof.

A method to reduce aSyn levels in a cell comprising contacting the cell with a therapeutic amount of pre-smiR-7-2 (SNCA) (SEQ ID NO:40, or 42), pre-smiR-153-1 (SNCA) (SEQ ID NO: 6, or 8), pre-smiR-495(SNCA) (SEQ ID NO:48, or 50), or any combination thereof.

A method to treat Parkinson's Disease in a subject in need thereof comprising administering to a subject in need thereof a therapeutic amount of pre-smiR-7-2(SNCA) (SEQ ID NO:40, or 42), pre-smiR-153-1 (SNCA) (SEQ ID NO: 6, or 8), pre-smiR-495(SNCA) (SEQ ID NO:48, or 50), or any combination thereof.

A method to rescue or increase survival of dopaminergic neurons in a subject in need thereof comprising administering to a subject in need thereof a therapeutic amount of pre-smiR-7-2(SNCA) (SEQ ID NO:40, or 42), pre-smiR-153-1 (SNCA) (SEQ ID NO: 6, or 8), pre-smiR-495(SNCA) (SEQ ID NO:48, or 50), or any combination thereof.

A method to rescue or increase survival of a dopaminergic neuron comprising contacting the neuron with a therapeutic amount of pre-smiR-7-2(SNCA) (SEQ ID NO:40, or 42), pre-smiR-153-1 (SNCA) (SEQ ID NO: 6, or 8), pre-smiR-495(SNCA) (SEQ ID NO:48, or 50), or any combination thereof.

A method to reduce APP levels in a subject in need thereof comprising administering to a subject in need thereof a therapeutic amount of pre-smiR-106(a)(APP) (SEQ ID NO:24, or 26), pre-smiR-153(APP) (SEQ ID NO:16, or 18), pre-smiR-101-1 (APP) (SEQ ID NO:12, or 14), or any combination thereof.

A method to reduce APP levels in a cell comprising contacting a cell with a therapeutic amount of pre-smiR-106(a) (APP) (SEQ ID NO:24, or 26), pre-smiR-153(APP) (SEQ ID NO:16, or 18), pre-smiR-101-1 (APP) (SEQ ID NO:12, or 14), or any combination thereof.

A method to treat Alzheimer's disease in a subject in need thereof comprising administering to a subject in need thereof a therapeutic amount of pre-smiR-106(a)(APP) (SEQ ID NO:24, or 26), pre-smiR-153(APP) (SEQ ID NO:16, or 18), pre-smiR-101-1 (APP) (SEQ ID NO:12, or 14), or any combination thereof.

In certain embodiments of the invention, the pre-smiRNA is administered by any suitable method, for example but not limited by intracerebral injection.

In certain aspect, the invention provides a method to regulate or reduce the levels of a first mRNA of geneY or its corresponding proteinY in a cell, wherein the first mRNA of geneY is regulated by an endogenous miR-XXX, comprising contacting the cell with a pre-smiR-XXX (geneY) the invention.

In certain aspects, the invention provides a method to treat a disease or disorder associated with increases levels of a first mRNA of geneY or its corresponding protein Y in a cell or a subject in need thereof, wherein the first mRNA is regulated by an endogenous miR-XXX, comprising contacting the cell or administering to the subject the pre-smiR-XXX (geneY) of the invention. In certain embodiment, the disease or disorder is neurodegenerative disease or disorder.

In certain aspects, the invention provides a method to modify a mammalian pre-miR-XXX comprising the following steps: Designing the miRNA-XXX and/or miRNA*-XXX sequence of a candidate endogenous pre-miR-XXX sequence to fully complement a first target sequence comprised in a first gene; thereby making a modified pre-smiR-XXX sequence.

In certain aspects, the invention provides a method to design a pre-smiR-XXX by modifying a mammalian pre-smiR-XXX comprising the following steps: Identifying a first target sequence comprised in a first gene which is targeted by a pre-miR-XXX; Modifying the pre-miR-XXX sequence, thereby designing a pre-smiR-XXX comprising in the 5' to 3' direction: G(n)-[Nm] which comprises [smiRNA-XXX]-[Ns] which is the loop sequence of a corresponding endogenous pre-miR-XXX-[N*r] which comprises [smiRNA*-XXX]-UU, or [Gn]-[N*r] which comprises [smiRNA*-XXX]-[Ns], which is the loop sequence of a corresponding endogenous pre-miR-XXX-[Nm] which comprises [smiRNA-XXX]-UU, wherein n=0-5, s, m and r are determined by the sequences in the endogenous pre-miR-XXX stem-loop; wherein the smiRNA-XXX is designed to complement, for example fully, the first target sequence. The method may optionally comprise a step of identifying a candidate pre-miR-XXX sequence. In certain embodiments of the method, smiRNA-XXX and smiRNA*-XXX fully complement each other. In certain embodiments of the method, smiRNA*-XXX is complementary to smiRNA-XXX sequence except that there are bulges present in the smiRNA-XXX/smiRNA*-XXX stem of the stem-loop structure, wherein the bulges are at the position of the bulges in the endogenous miRNA-XXX/miRNA*-XXX stem-loop structure. In certain aspects, the invention provides a pre-smiRNA-XXX made by the methods described herein.

In certain aspects, the invention provides endogenous miRNAs that regulate alpha Synuclein gene expression within midbrain dopamine neurons. The invention also provides modified miRNAs which are based on these endogenous miRNAs. The potency of these miRNAs is compared in vitro, wherein the miRNAs are evaluated individually or in combinations. In another aspect, the invention provides methods for brain delivery of the inventive compositions. In certain non-limiting embodiments, the invention discloses methods for brain delivery in animal model. Suitable animal models are known in the art, and include without limitation the PAC wild-type and A53T alpha Synuclein transgenic mouse models.

In another aspect, the invention provides modified miRNAs, including but not limited to a modified miR-153 sequence, linked to an RVG-9R peptide (smiR-153/RVG-9R), which can reduce alpha Synuclein accumulation throughout the striatum. In certain embodiments, no evidence of inflammation is observed by standard Nissl staining approaches when the modified miRNAs of the invention, including but not limited to smiR-153/RVG-9R, are used to reduce accumulation of a target gene.

In certain embodiments, the invention provides methods which determine target gene, for example but not limited to SNCA, expression or accumulation, specificity of the modified miRNAs of the invention in terms of alteration of expression of other targets, analysis of motor behavior, inflammation, or toxicology analysis.

In certain aspects the invention provides optimized miRNA sequences (smiRNAs). In certain embodiments these smiRNAs are based on endogenous miRNAs. In certain embodiments, the optimized miRNAs of the invention are generated in vitro. In certain embodiments the modified miRNAs are single strand optimized. In other embodiments, the modified miRNAs are double strand optimized. In certain embodiments, the optimized miRNA sequences are mammalian. In other embodiments, the optimized miRNAs are human. In certain embodiments, the starting miRNA is human. In certain embodiments, the optimized miRNAs of the invention target the 3'UTR of a human gene of interest.

In certain embodiments, the optimized miRNAs of the invention have reduced off target toxicity, which is an undesired, deleterious or unintended effect observed in a cell which expresses miRNA. In certain embodiments, the optimized miRNAs of the invention have increased specificity towards a target gene of interest, wherein the target gene of interest is a target of the endogenous miRNA.

In certain aspects the invention excludes inhibitory RNAs which target sequence is not based on an endogenous miRNA target sequence within a gene of interest. In certain aspects the invention excludes inhibitory RNAs which target sequence is not located within the 3'UTR of a gene of interest. In certain aspects the invention excludes inhibitory RNAs which are not based on an endogenous miRNA.

In other aspects the invention provides methods to design and generate modified miRNAs.

In other aspects the invention provides methods to reduce a first protein and/or gene levels of expression and/or accumulation, comprising administering a modified miRNA of the invention which targets the first gene.

In certain aspects the invention provides modified miRNAs which regulate genes, for example but not limited to alpha Synuclein, APP, and Tau, which are implicated in neurodegenerative diseases or disorders. In non-limiting examples, a miR-153 target site, is present in the aSynuclein 3'UTR, and in APP 3'UTR. In one aspect the invention provides modified miR-153 sequences towards the APP sequence. In another aspect, the invention provides modified miR-153 sequences towards alpha Synuclein. The 3' UTRs of APP and alpha Synuclein are different from each. The invention provides optimized miRNAs with specificity towards different natural targets. In certain embodiments, there is one starting miRNA which is optimized for specificity towards different natural targets.

In one aspect the invention provides modified miRNA101, miRNA106a, miRNA496, miRNA660, miRNA656, miRNA374, miRNA495, miRNA153 which are ss or ds modified toward 3'UTR of APP. In another aspect, the invention provides modified miRNA-153, miRNA-7-2, miRNA-495 which are ss or ds modified toward 3'UTR of alpha Synuclein. In certain embodiments, APP and alpha Synuclein are human. In other embodiments, miRNA101, miRNA106a, miRNA496, miRNA660, miRNA656, miRNA374, miRNA495, miRNA-153-1, miRNA-7-2, are human.

In certain embodiments the modified pre-miRNAs of the invention do not trigger interferon response. In certain embodiments the modified pre-miRNAs of the invention do not trigger inflammation in the subject.

In another aspect, the invention provides a method to make a mammalian smir-XXX comprising the following steps: chemically synthesizing, or in vitro transcribing, or making by recombinant methods the mammalian pre-smiR-XXX of the invention, wherein the miRNA-XXX and/or miRNA*XXX sequences are fully complementary to a first target sequence comprised in a first gene. In certain embodiments, the mammalian pre-smiR-XXX of the invention are purified, or treated with a phosphatase.

In certain aspects, the invention provides the discovery of miRNA pathways regulating aSynuclein expression in dopaminergic neurons which affords the use of these pathways for PD therapy. In another aspect, the invention provides candidates miRNAs for regulating endogenous aSynuclein. In certain aspects, the candidate miRNAs are identified by bioinformatics investigation. In other aspects, the invention provides in vitro data on ES cell derived cultures of dopaminergic neurons to confirmed the efficacy of various endogenous miRNAs and modified miRNAs in suppressing aSynuclein, or APP expression. In another aspect, the invention provides that sequence optimization of the endogenous miRNA constructs yielded increased efficiency in aSynuclein suppression. In another aspect, the invention provides that in vivo studies on transgenic mice expressing human aSynuclein demonstrated a 70% decrease in aSynuclein levels upon delivery of one of the constructs.

The invention provides methods for delivery of the miRNAs of the invention, which can be achieved through intracerebral injection of the miRNA complexed with the RVG-9R peptide, which confers neuronal specificity.

The invention provides modified miRNAs which affect target gene transcription or translation utilizing the endogenous system, which processes the endogenous miRNAs. Piggy-backing on an endogenous system yields advantages, including: (1) the limitation of side effects arising from the introduction of synthetic constructs, and (2) higher efficiency due to the propensity of miRNA to recruit additional regulatory elements.

BRIEF DESCRIPTION OF THE FIGURES

FIG. 11 discloses SEQ ID NOS: 108, 108, 108, 95, 108, and 95, respectively, in order of appearance.

DETAILED DESCRIPTION OF THE INVENTION

Figure 1A:
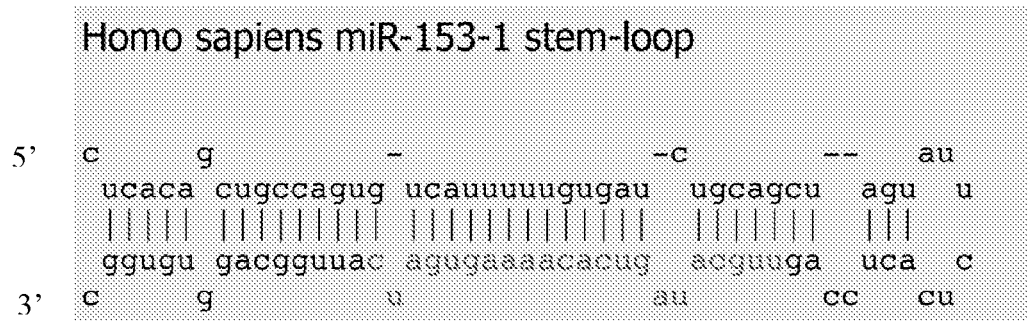
FIG. 1 shows: A, Stem-loop structure of human miR-153 precursor (WWW.mirbase.org) ((SEQ ID NO:91); the mature miR-153 (Magenta) and the imperfect complement (miR-153*) lead to 2 nucleotide bulges. B, Modest complementarity of miR-153 (SEQ ID NO:20) to aSynuclein 3'UTR (SEQ ID NO:93) (SNCA, in this case mouse; from Doxakis et al., 2010).

The terms "treatment" or "treat" as used herein include treating, preventing, ameliorating, and/or decreasing the severity of the symptoms of a disease or disorder, or improving prognosis for recovery.

The term "nucleotide" refers to a ribonucleotide or a deoxyribonucleotide. In certain embodiment the nucleotide is a modified form thereof, or an analog thereof. Nucleotides may include species that comprise purines, e.g., adenine, hypoxanthine, guanine, and their derivatives and analogs, as well as pyrimidines, e.g., cytosine, uracil, thymine, and their derivatives and analogs.

The terms modified miRNA, optimized miRNA, perfected miRNA or synthetic miRNA are used interchangeably.

mir-XXX is the pre-miRNA sequence, which can be either in linear form or in secondary, or tertiary structure. "XXX" refers to the specific number corresponding to the endogenous miRNA.

Modified pre-miRNAs or miRNAs of the invention carry the prefix "s", "ss" or "ds" to distinguish them from the corresponding endogenous pre-miRNA or miRNA sequences. For example, smiR-XXX indicates a modified sequence which is originally based on the endogenous miR- XXX sequence. Single-strand "ss" modified miRNA, also referred to as ss-perfected, indicates a modified miRNA-XXX sequence which is fully complementary to the target sequence in gene Y recognized by an endogenous miRNA, and wherein the miRNA*-XXX sequence is fully complementary to the miRNA-XXX sequence, except that the bulges in the miRNA-XXX/miRNA*-XXX stem are maintained at their respective position in the endogenous pre-miRNA.

Double-strand "ds" modified miRNA, also referred to as ds-perfected, indicates a modified miRNA-XXX sequence which is fully complementary to the target sequence in gene Y recognized by an endogenous miRNA, and wherein the miRNA*-XXX sequence is fully complementary to the miRNA-XXX sequence.

miRNA-XXX is used interchangeably with miR-XXX and indicates the mature miRNA which is more commonly associated with the RISC complex.

miRNA*-XXX is used interchangeably with miR*-XXX and indicates the mature miRNA which is incorporated less often in the RISC complex.

microRNAs originating from the 3' or 5' end of a pre-miRNA are denoted with a -3p or -5p suffix, such as miRNA-XXX-3p and miRNA-XXX-5p.

Throughout the specification, miR, miRNA, and pre-miRNA may be used interchangeably.

Nucleotide analogs include nucleotides having modifications in the chemical structure of the base, sugar and/or phosphate, including, but not limited to, 5-position pyrimidine modifications, 8-position purine modifications, modifications at cytosine exocyclic amines, and substitution of 5-bromo-uracil; and 2'-position sugar modifications, including but not limited to, sugar-modified ribonucleotides in which the 2'-OH is replaced by a group such as an H, OR, R, halo, SH, SR, $NH_2$, NHR, $NR_2$, or CN, wherein R is an alkyl moiety. Nucleotide analogs are also meant to include nucleotides with bases such as inosine, queuosine, xanthine, sugars such as 2'-methyl ribose, non-natural phosphodiester linkages such as methylphosphonates, phosphorothioates and peptides.

RNA interference (RNAi) or silencing refers to the process of sequence-specific post-transcriptional gene regulation in eukaryotes which is mediated by small RNAs. Small RNA molecules have emerged as critical regulators of gene expression and function in eukaryotic genomes. Two primary categories of small RNAs which are involved in RNA interference are short interfering RNAs (siRNAs) and microRNAs (miRNAs) (for example see Carthew and Sontheimer, 2009, "Origins and Mechanisms of miRNAs and siRNAs". Cell 136, 642-655.).

Databases of miRNAs and algorithms to predict target sequences and genes are known. Non-limiting example is the miRBase, which is a searchable database of published miRNA sequences and annotation. Each entry in the miR-Base Sequence database represents a predicted hairpin portion of a miRNA transcript (termed mir in the database), with information on the location and sequence of the mature miRNA sequence (termed miR) miRBase can link miRNAs to targets predicted by microCosm, TargetScan and Pictar prediction tools. For example but not limited, TargetScan is a tool that computationally predicts targets sequences which are targeted by the endogenous miRNAs. For example but not limited, a number of endogenous miRNAs are predicted computationally by the TargetScan website to hit APP 3'UTR, or alpha Synuclein 3 UTR. In certain embodiments, computational tools and predictions identify homology between the mature miRNA sequence and the sequence, for example the 3'UTR, of the target gene. In certain embodiments, these computation prediction are validated by various assays, for example but not limited in vitro using a luciferase assay, or any other suitable biological assay.

Figure 10:
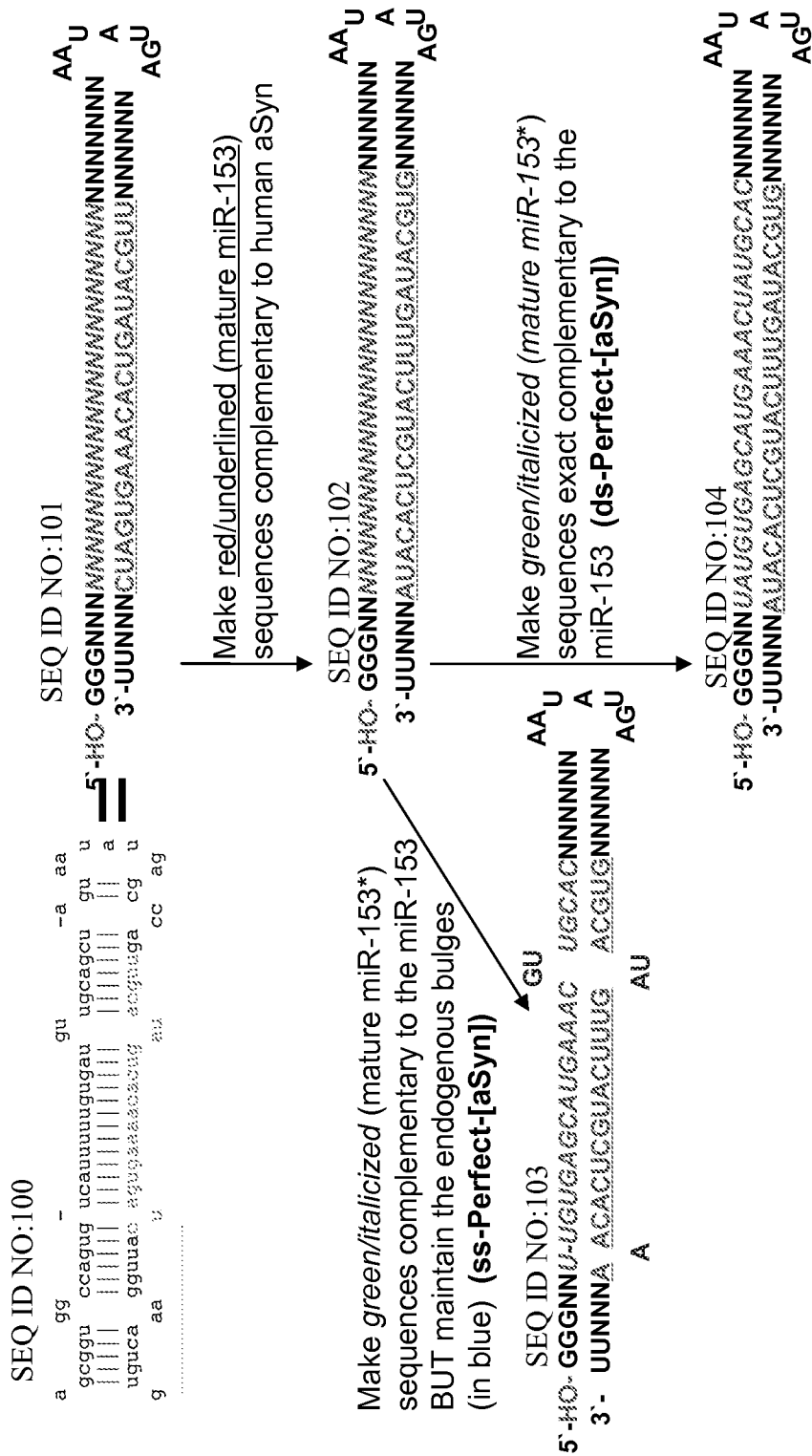
FIG. 10 shows one embodiment of a method to optimize miR-153-2. This figure uses miR153-2 as the starting endogenous miRNA in a non-limiting example which shows how to optimize an endogenous miRNA toward a target 3'UTR of a gene of interest, in this example human alpha Synuclein.
Figure 11:
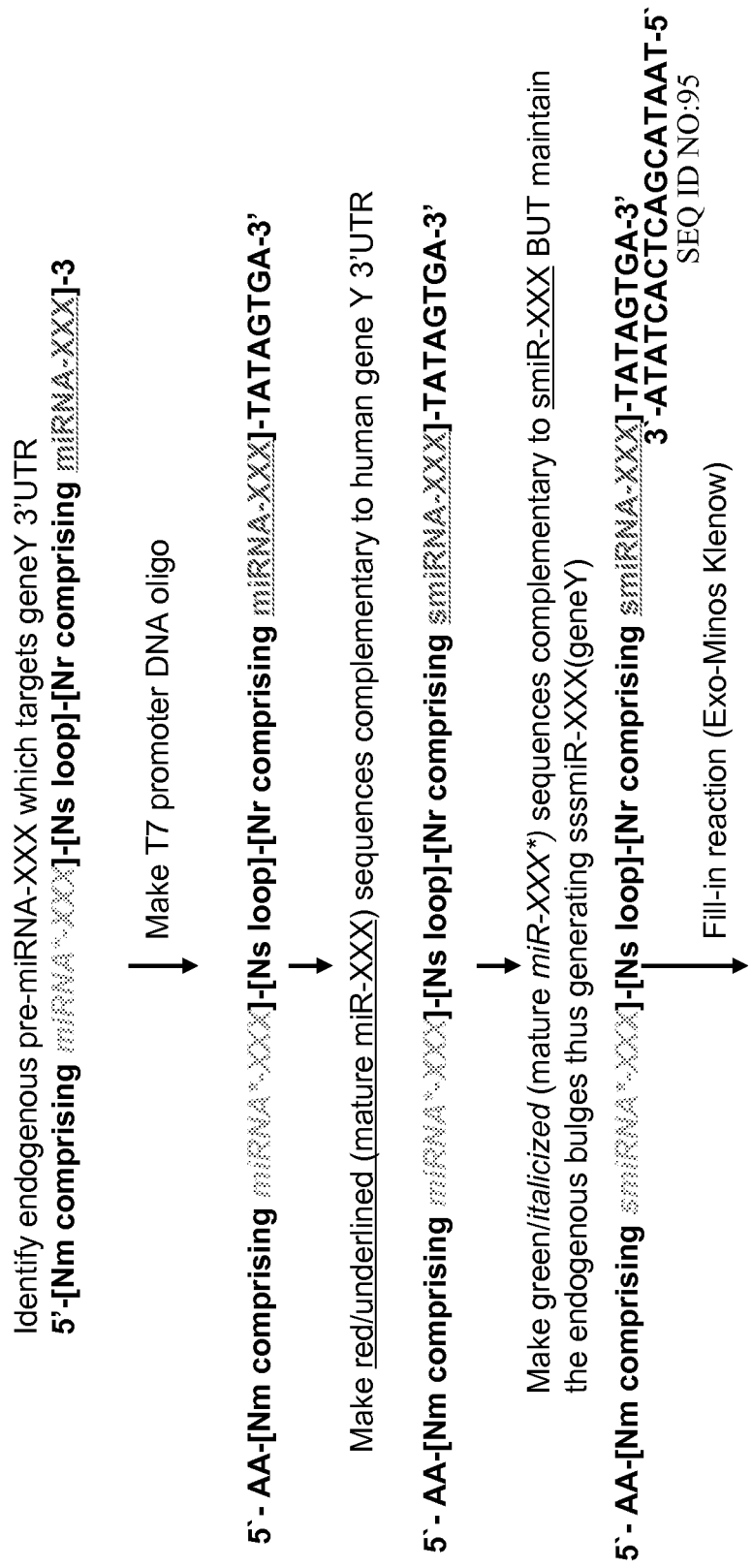
FIG. 11 shows a non-limiting embodiment of design and synthesis of a single strand modified pre-miRNA targeting gene Y referred to as sssmiR-XXX (geneY). As explained throughout the text, an endogenous pre-miRNA is identified from a database which lists computational and/or confirmed pre-miRNA sequences. A non-limiting example of such database is miRBase. Using any one of a number of computational prediction tools, potential targets of the endogenous pre-miRNA are identified. In a non-limiting example, any one of these computational targets may be analyzed or confirmed in a biological study. Once a potential target is identified a given pre-miRNA, for example but not limited to geneY, the endogenous pre-miRNA is modified and synthesized as schematically represented in this FIG. 11, or as described throughout the specification. In this non-limiting example the mature miRNA is in the 3' end of the pre-miRNA sequence. The invention also contemplates design and synthesis of modified miRNAs wherein the mature miRNA is located in the 5' end of the pre-miRNA. The invention also contemplates design and synthesis of modified miRNAs wherein mature miRNAs are located in both the 5' and 3' ends of the pre-miRNA. In certain embodiments, in order to maintain the bulges at the positions of the endogenous miRNA, the sequence of miRNA* is modified so as to maintain the position of these bulges. The pre-smiRNA-XXX (geneY) is delivered to the cell by any suitable method, and is processed by the edogenous system to mature smiRNA-XXX (geneY).
Figure 11:
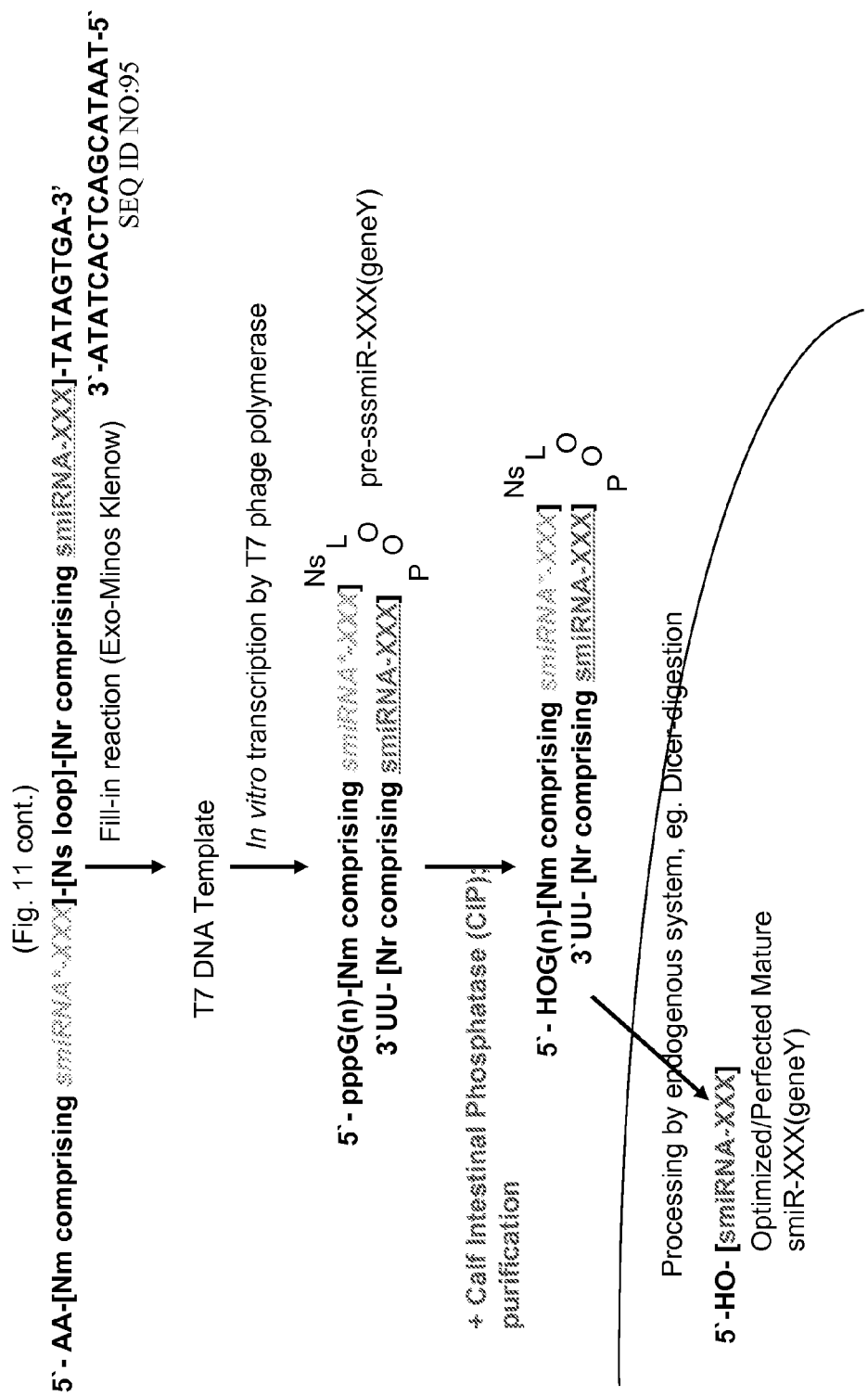

In certain embodiments, perfected miRNA is miRNA which have the general structure of the pre-miRNA, but is modified in the miRNA part (for example see FIG. 10 describing steps of modifying endogenous miR153-2) to perfectly complement the target, for example but not limited to alpha Synuclein. Thus perfected miRNAs of the invention are different from endogenous miRNA which usually are weakly complementary to their target, with only 7-8 bases being matched to the target.

Pri-miRNAs and pre-miRNAs have hairpins, with a second strand complementary to the mature miRNA. In certain embodiments, the second strand is made perfectly complementary to the new miRNA to make a perfect stem loop (ds-perfected), or it is kept imperfect by adding a couple of bulges (ss-perfected). A non-limiting example is the natural form of pri-mir-153 or pre-miR-153, which has a couple of bulges. In certain embodiments, in vitro, the ds-perfected is more effective.

The modified miRNAs of the invention are different from sh-RNAs, which are simply artificial hairpins. Some viral vectors have been used to deliver more sophisticated shR-NAs, that include sections of pre-miRNAs from other pre-miRNAs, because the bulges and loops are thought to help. Modified miRNAs of the invention target sequence which is normally targeted by an endogenous miRNA. Typically the target sequence is within the 3'UTR of a gene. Thus, modified miRNAs of the invention are different from other inhibitory RNAs, such as shRNAs which target any randomly selected region of a gene of interest.

In certain aspects the invention provides modified miRNA, made by a method where the starting point is the natural miRNA, wherein the natural miRNA is perfected as described herein, for added specificity and potency. This is for a few reasons: (i.) The 'natural' target site on a 3'UTR is probably better than novel artificial sites that are generated based on computational approaches: for instance, the alpha Synuclein 3'UTR target sequence for mir-153 is probably exposed in a particularly advantageous way, and thus targeting this sequence exactly, but with an improved reagent, maybe advantageous compared to using a shRNA, a target site which is randomly selected, or a target site is designed by a computational approach. (ii.) The secondary and tertiary structure of the natural miRNA is probably better preserved in 'perfected' pre-miRNAs, rather than with shRNAs that may or may not incorporate a few features from some pri-miRNA. (iii.) There are data suggesting that 'unnatural' approaches with siRNA are more toxic than naturally occurring ones.

In certain aspects, the invention provides synthetic miRNA as described herein. Such synthetic miRNAs are useful in gene therapy, for example but not limited to neuroprotective gene therapy for, for example but not limited to therapy for PD patients. The specific optimized miRNA constructs in of the invention could be formulated and used as pharmaceutical agents.

In certain embodiments of the methods for making the modified miRNAs of the invention, one step is a computational evaluation of the 'perfected' pre-miRNAs to make sure they do not hit other target genes. In certain embodiments, this is a non-limiting example of reducing the off-target toxicity of modified miRNAs of the invention.

In certain aspects, the invention provides modified miR-NAs, specifically smiR153, which are based on miR153-1 and miR153-2. In certain aspects, the invention provides methods to treat neurodegenerative disorders or diseases, using modified miR153 sequences. Endogenous and modified miR-153 sequence target APP or aSynuclein. APP and aSynuclein are central proteins in the two main forms of human neurodegeneration, Alzheimer's disease and Parkinson's disease. The miR-153 sequences are optimized differently—in one case to match APP, in the other case to match aSynuclein. But this allows to use the same "core" mir-153 structure for the RNA therapeutic in both cases, as each miR has a unique 3-dimensional structure, which may affect stability and delivery approaches in vivo.

In certain embodiments, the modified miR153 sequence target 3'UTR target sequence in alpha Synuclein, Tau, or APP. In certain embodiments, alpha Synuclein is targeted by the modified miR153(SNCA) as described herein. In other embodiments, APP is targeted by the modified miR153(APP) as described herein In certain aspects, the invention provides modified miRNA, ss or ds modified miRNAs, which are based for example but not limited on human miR-7-2, miR-101, miR-106a, miR-153-1 and miR-153-2, miR-495.

In certain embodiments the invention provides methods to reduce or modulate the levels of a target protein using the RNAi therapeutics of the invention. In certain embodiments, the methods treat a disease or disorder associated with accumulation and/or increased levels of a target protein or its mRNA. In certain embodiments, the methods comprise administering to a subject in need thereof, or to a specific organ, including but not limited to the brain, or to a specific tissue or cell, a therapeutic amount of the modified miRNAs of the invention so as to reduce the levels of a target protein.

In certain embodiments, the disease or disorder is a neurodegenerative disease or disorder. For example but not limited, provided are methods to reduce levels of aSynuclein, which is associated with PD. The instant modified miRNAs are also useful in methods to treat other neurodegenerative diseases or disorders, for example but not limited to Alzheimer's disease, by reduction of APP levels. The instant methods may be advantageous, as antibodies may not work as well, because they only reduce the Abeta species extracellularly.

The present invention provides methods of suppressing or reducing the accumulation of a target protein, for example but not limited to alpha Synuclein, APP or Tau, in a cell by introducing a nucleic acid molecules (e.g., modified miRNAs described herein) into the cell in an amount sufficient to suppress accumulation of the target protein in the cell. In certain embodiments, the accumulation is suppressed by 10%, 20%, 30%, 40%, 50%, 60%, 70%, 80%, 90% 95%, or 99%. In certain embodiments, the accumulation is suppressed by at least 10%, 20%, 30%, 40%, 50%, 60%, 70%, 80%, 90% 95%, or 99%. In certain embodiments, the accumulation is suppressed by about 10%, 20%, 30%, 40%, 50%, 60%, 70%, 80%, 90% 95%, or 99%. In certain embodiments, the suppression of the accumulation of the protein is in an amount sufficient to cause a therapeutic effect.

The present invention provides a method of preventing cytotoxic effects of a protein, mutant or wild-type, in a cell by introducing a nucleic acid molecules (e.g., a ribonucleic acid (RNA)) described herein into the cell in an amount sufficient to suppress accumulation of the protein. In certain embodiments, the nucleic acid molecules prevents cytotoxic effects of the protein, e.g., in a neuronal cell. In certain embodiments, the modified miRNAs of the invention prevent cytotoxic effects of protein in neurodegenerative diseases or disorders.

The present invention provides a method to inhibit expression of a target protein in a cell by introducing a nucleic acid molecule (e.g., a ribonucleic acid (RNA)) described herein into the cell in an amount sufficient to inhibit expression of the protein, and wherein the RNA inhibits expression, transcription and/or translation, of the gene encoding the target protein. In certain embodiments, the protein is inhibited by at least 10%, 20%, 30%, 40%, 50%, 60%, 70%, 80%, 90% 95%, or 99%. In certain embodiments, the inhibition is at a level sufficient to treat a disease or disorder associated with the target protein, or any variant thereof.

The present invention provides a method to inhibit expression of a target gene, for example but not limited to alpha synuclein, APP or Tau gene in a mammal (e.g., a human or a non-human mammal) by (a) contacting a mammal containing a neuronal cell, wherein the neuronal cell contains the gene of interest and the neuronal cell is susceptible to RNA interference, and the gene is expressed in the neuronal cell, with a ribonucleic acid (RNA) or a vector described herein, thereby inhibiting expression of the gene. In certain embodiments, the accumulation of is suppressed by at least 10%. In certain embodiments, the target gene is inhibited by at least 10%, 20%, 30%, 40%, 50%, 60%, 70%, 80%, 90% 95%, or 99%. In certain embodiments, the cell is located in vivo in a mammal.

The present invention provides a viral vector comprising a promoter and a micro RNA (miRNA) shuttle containing an embedded siRNA specific for a target sequence. In certain embodiments, the promoter is an inducible promoter. In certain embodiments, the vector is an adenoviral, lentiviral, adeno-associated viral (AAV), poliovirus, HSV, or murine Maloney-based viral vector. In certain embodiments, the targeted sequence is a sequence associated with a condition amenable to siRNA therapy, such as a neurodegenerative disease.

In other embodiments, the invention provides synthetic modified miRNAs as described which are synthesized and purified in vitro. In certain embodiments, the synthetic modified miRNAs do not lead to inflammation as a consequence of the administration of the modified miRNA.

The present invention provides a method of preventing cytotoxic effects of neurodegenerative disease in a mammal in need thereof, by introducing the vector encoding a miRNA described herein into a cell in an amount sufficient to suppress accumulation of a protein associated with the neurodegenerative disease, and wherein the RNA prevents cytotoxic effects of neurodegenerative disease.

The present invention also provides a method to inhibit expression of a protein associated with a neurodegenerative disease in a mammal in need thereof, by introducing the vector encoding a miRNA described herein into a cell in an amount sufficient to inhibit expression of the protein associated with the neurodegenerative disease, wherein the RNA inhibits expression of the protein associated with the neurodegenerative disease. The protein associated with the neurodegenerative disease is inhibited by at least 10%, 20%, 30%, 40%, 50%, 60%, 70%, 80%, 90% 95%, or 99%.

In one aspect, the invention relates to compounds, compositions, and methods useful for modulating gene expression associated with neurodegenerative disease or disorder, using short RNA interfering molecules, specifically the modified miRNAs of the invention. A modified miRNA molecule of the instant invention can be produced by any suitable methods, e.g., chemically synthesized, expressed from a vector, enzymatically synthesized, or any combination thereof.

In certain embodiments of the present invention, the alleles of the targeted gene may differ by seven or fewer nucleotides (e.g., 7, 6, 5, 4, 3, 2 or 1 nucleotides). For example the alleles may differ by only one nucleotide. Examples of targeted gene transcripts include transcripts encoding alpha Synuclein, Tau, or beta-amyloid precursor protein (betaAPP or APP). The targeted genes and gene products (i.e., a transcript or protein)

may be from different species of organisms, such as a mouse allele or a human allele of a target gene. In certain embodiments, the targeted genes are specifically human genes. In certain embodiments, the modified miRNA is a human miRNA.

"Neurological disease" and "neurological disorder" refer to both hereditary and sporadic conditions that are characterized by nervous system dysfunction, and which may be associated with atrophy of the affected central or peripheral nervous system structures, or loss of function without atrophy. A neurological disease or disorder that results in atrophy is commonly called a "neurodegenerative disease" or "neurodegenerative disorder." Neurodegenerative diseases and disorders include, but are not limited to, amyotrophic lateral sclerosis (ALS), hereditary spastic hemiplegia, primary lateral sclerosis, spinal muscular atrophy, Kennedy's disease, Alzheimer's disease, Parkinson's disease, multiple sclerosis, and repeat expansion neurodegenerative diseases, e.g., diseases associated with expansions of trinucleotide repeats such as polyglutamine (polyQ) repeat diseases, e.g., Huntington's disease (HD), spinocerebellar ataxia (SCA1, SCA2, SCA3, SCA6, SCAT, and SCA17), spinal and bulbar muscular atrophy (SBMA), dentatorubropallidoluysian atrophy (DRPLA). An example of a disabling neurological disorder that does not appear to result in atrophy is DYT1 dystonia. The gene of interest may encode a ligand for a chemokine involved in the migration of a cancer cell, or a chemokine receptor.

The present invention further provides a method of substantially silencing a target gene of interest or targeted allele for the gene of interest in order to provide a therapeutic effect. As used herein the term "substantially silencing" or "substantially silenced" refers to decreasing, reducing, or inhibiting the expression of the target gene or target allele by at least about 5%, 10%, 15%, 20%, 25%, 30%, 35%, 40%, 45%, 50%, 55%, 60%, 65%, 70%, 75%, 80%, 85% to 100%.

In one embodiment, the present invention further provides a method of substantially silencing both alleles (e.g., both mutant and wild type alleles) of a target gene. In certain embodiments, the targeting of both alleles of a gene target of interest can confer a therapeutic effect by allowing a certain level of continued expression of the wild-type allele while at the same time inhibiting expression of the mutant (e.g., disease associated) allele at a level that provides a therapeutic effect.

In one embodiment, the present invention further provides a method of substantially silencing a target allele while allowing expression of a wild-type allele.

Synthesis of Modified miRNAs of the Invention

The modified miRNAs of the invention are synthesized by any suitable method. Various such methods are known in the art. In certain embodiments, the modified miRNAs are made by chemical synthesis of the RNA. In certain embodiments, the modified miRNAs are made by in vitro synthetic reaction. In certain embodiments, the modified miRNAs are made by in vitro transcription, for example but not limited by use of transcription kits to generate the material (e.g. T7 kit from Epicentre). Modified miRNA could be generated in vitro as well. In certain embodiments, the modified miRNA of the invention may be synthesized by a protocols as described in Gondai et al. the contents of which is hereby incorporated by reference in its entirety. In certain embodiments, the transcription product, for example but not limited to the T7 product, is purified using standard Qiagen columns and sephadex columns. Other methods for purifying nucleic acids are suitable. Such methods are known in the art.

In certain embodiments, methods include dephosphorylating the product, for example but not limited with CIP. In certain embodiments, the methods include addition of several Guanines (1,2,3,4,5), for example but not limited to the 5' end of the miRNA. In certain embodiments, the addition of Guanines avoids the interferon response, such that effectively there is not inflammation.

Formulations and Delivery of the RNAi Therapeutics of the Invention.

A therapeutic amount or dose refers to that amount of an inhibitory RNA, as an active ingredient, designed to inhibit the expression of a target gene. In certain embodiments, the inhibitory RNA is useful to treat, prevent and/or ameliorate pathological conditions. Therapeutic effect refers to a change in the associated abnormalities of the disease state, including pathological and behavioral deficits; a change in the time to progression of the disease state; a reduction, lessening, or alteration of a symptom of the disease; or an improvement in the quality of life of the person afflicted with the disease. Therapeutic effects can be measured quantitatively by a physician or qualitatively by a patient afflicted with the disease state targeted by the RNAi.

In certain embodiments, the pathological condition is associated with alpha Synuclein expression. In certain embodiments, the pathological condition is associated with expression of APP. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between toxic and therapeutic effects is the therapeutic index, and it can be expressed as the ratio, LD50/ED50. Pharmaceutical compositions that exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact amount will be determined by the practitioner, in light of factors related to the subject that requires treatment. Amount and administration are adjusted to provide sufficient levels of the active ingredient or to maintain the desired effect. Factors that may be taken into account include the severity of the disease state, location of the affected tissue or cells within the body, general health of the subject, age, weight, and gender of the subject, diet, time and frequency of administration, drug combination(s), reaction sensitivities, and tolerance/response to therapy.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ formulations suitable for the smiRNAs of the invention. Those skilled in the art will employ delivery methods suitable for the formulations of the smiRNAs of the invention.

Delivery methods of the RNAi therapeutics can be tailored to particular cells or tissues, disease or conditions, locations of affected diseases organ, tissue or cell, and other relevant factors.

Various methods for delivery of RNAi therapeutics, including cell and tissue specific delivery, are known in the art and under development. See e.g., Lu P Y, Woodle M C.: "Delivering small interfering RNA for novel therapeutics" Methods Mol. Biol. 2008; 437:93-107, and references cited therein; Saghir Akhtar and Ibrahim F. Benter: "Nonviral delivery of synthetic siRNAs in vivo" *J. Clin. Invest.* 117(12): 3623-3632 (2007); Huricha Baigude, Dr., Tariq M. Rana "Delivery of Therapeutic RNAi by Nanovehicles", *ChemBioChem*. Volume 10 Issue 15, Pages 2449-2454; Keller M. "Nanomedicinal delivery approaches for therapeutic siRNA." Int J. Pharm. 2009 Sep. 11; 379(2):210-1; Meade B R, Dowdy S F. "The road to therapeutic RNA interference (RNAi): Tackling the 800 pound siRNA delivery gorilla." Discov Med. 2009 December; 8(43):253-6.

In non-limiting examples, the RNAi therapeutics of the invention may be delivered by suitable vectors which comprise nucleic acids encoding the smiRNAs of the invention. In other embodiments, delivery of the RNAi therapeutics is lipid and lipid-like materials mediated. See e.g., Akin Akinc et al. "Development of Lipidoid-siRNA Formulations for Systemic Delivery to the Liver", *Molecular Therapy* (2009) 175, 872-879. In other embodiments, the RNAi therapeutics are delivered as chemically modified or otherwise modified molecules, such that their in vivo targeting and/or stability is improved.

In certain embodiment, the RNAi therapeutic compositions of the invention are used for treatment of neurological diseases or disorders. For methods of delivery of RNAi therapeutics to the brain, see e.g. William M. Pardridge "shRNA and siRNA delivery to the brain" *Advanced Drug Delivery Reviews*, Volume 59, Issues 2-3, 30 Mar. 2007, Pages 141-152; Saroj P Mathupala, "Delivery of small-interfering RNA (siRNA) to the brain" *Expert Opinion on Therapeutic Patents*, February 2009, Vol. 19, No. 2, Pages 137-140; PCT Publication WO2008033285.

In certain embodiments of the therapeutic methods, the delivery approach uses rabies viral peptide/polyarginine peptide. See for example Kumar et al., (2007), the contents of which is hereby incorporated by reference in its entirety.

In certain embodiments, delivery is by intracerebral (intrastriatal) or intracerebroventricular injection. Without being bound by any theory, such intracerebral (intrastriatal) or intracerebroventricular appears more effective and requires less material for injection. Also, it is likely to lead to less inflammatory effect, and immune response. Repeated peripheral administration of a peptide may lead to neutralizing antibodies.

In other embodiments, the RNAi therapeutics of the invention are conjugated to suitable delivery vehicles, for example but not limited as modified miRNAs conjugated to peptide, for example but not limited to RVG-9R peptide.

In certain embodiments the RNAi therapeutics of the invention are formulated for delivery directly to the brain, for example but not limited to intracerebral delivery via injection, or cannula.

EXAMPLES

Example 1

Targeting Alpha Synuclein with Novel RNAi Therapeutics

Therapeutic Description:

In certain aspect the invention provides novel RNAi therapeutics for PD by targeting aSynuclein (aSyn). Previously, we indentified and evaluated endogenous miRNAs that regulate aSynuclein gene expression within midbrain dopamine neurons. See Example 2. In addition, we compared the potency of these miRNA leads, initially in vitro, individually or in combinations; and we explored brain delivery options for these in a rodent model detailed below. These studies have led to the development of a next-generation of miRNA-based therapies that appear efficacious in vivo, and are advantageous from a therapeutic development perspective than published approaches.

Provided herein are synthetic miRNAs (smiRNAs) that are delivered and dosed by stereotaxic intracerebral infusion. These smiRNAs are structurally similar to endogenous miRNAs, but have been computationally optimized to achieve specificity, in a non-limiting example for the aSyn 3'UTR. Surprisingly, such optimization proved to also highly increase the potency of these smiRNAs. These smiRNAs effectively suppress the accumulation of aSynuclein throughout the striatum, as described herein. Delivery of the modified miRNAs is enhanced using a short peptide derived from rabies virus glycoprotein that targets acetylcholine receptors, as well as a polyarginine stretch that stabilizes the RNA and further enhances cell uptake. Modified miRNAs conjugated to a peptide, and methods for their use, have not previously been described in the context of intracerebral dosing and delivery.

smiRNAs and other RNAi therapeutics can effectively reduce the production of aSynuclein protein.

Therapeutic Rationale:

(1.) aSynuclein protein expression level is a key determinant of risk for developing 'sporadic' PD, per recent GWAS studies.

(2.) The major hurdles that have hampered the development of aSynuclein RNAi therapeutics for PD are: potency, specificity, and delivery.

(3.) Reduced levels of aSynuclein appear to be well tolerated. Mice deficient in aSyn live a normal lifespan[2] and appear protected from certain dopaminergic toxins[3,4]; dopamine content and release are mildly altered in the context of complete loss of aSynuclein. There has been one study using AAV2 siRNA vectors, suggesting toxicity; a parsimonious interpretation of the toxicity associated with these AAV2 siRNA vectors is off-target effect[5].

(4.) Endogenous RNA interference (RNAi) is primarily established by MicroRNAs (miRNAs) miRNAs are evolutionarily conserved, non-protein coding transcripts that play an important function in post-transcriptional regulation of gene expression. Mature miRNAs, 18-25 nucleotides long, are typically processed from 50-100 nucleotide-long primary (precursor) transcripts by the Drosha and Dicer endonuclease complexes, consecutively. Mature miRNAs typically inhibit translation of their target[6]. First characterized in invertebrates, several hundred miRNAs have been identified in vertebrates, but only a few of them have been associated with specific cellular functions miRNAs have been identified that are expressed during differentiation to a neuronal phenotype and to control neuronal identity establishment, either in vivo or in vitro[7]. More recently we showed that miRNAs are needed for dopaminergic neurons maintenance in brain[1].

Figure 1B:
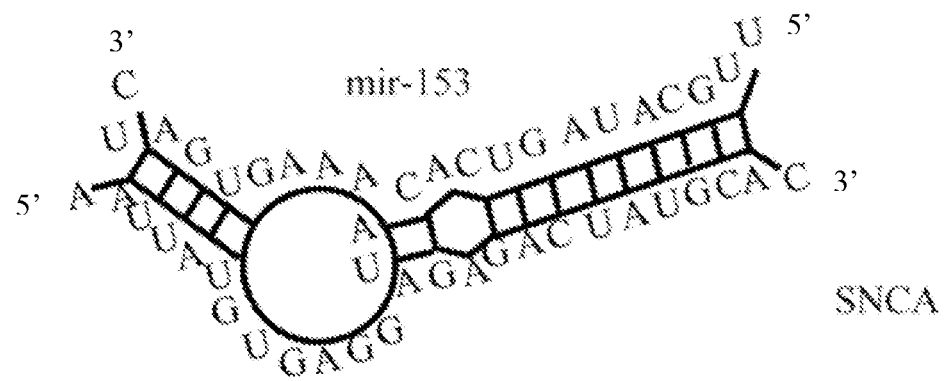

(5.) RNA interference as a therapeutic strategy has been pursued to reduce the expression of targeted genes in brain, primarily using synthetic short interfering RNA (siRNA) or short hairpin (shRNAs)[8]. siRNAs are short RNA duplexes that are perfect in their complementarity to one another; in contrast, miRNAs generated by cleavage with Dicer contain a non-complementary bulge with their complementary strand (miRNA*; FIG. 1). siRNAs typically guide cleavage of mRNA targets, whereas miRNAs typically inhibit translation of targets without mRNA cleavage[9]. An additional distinction is that miRNAs are typically quite degenerate, with hundreds of targets and very limited regions of complementarity to individual targets, whereas therapeutic siRNAs are typically designed for perfect matching to target. Nonetheless, there are at least two advantages to the use of miRNAs and modified miRNA, rather than artificial siRNAs or shRNAs, for gene silencing in vivo. First, miRNAs appear better tolerated by cells, as viral transduction of high levels of shRNA are reported to be toxic in liver[10] and brain[11] whereas miRNAs appear to mitigate this. miRNAs are part of an endogenous gene regulation process. Second, miRNA target sites on mRNA 3'UTRs are likely to have a tertiary structure permitting the access of regulatory elements. However, existing approaches for miRNA therapy suffer from major limitations: they lack specificity, and delivery has only previously been achieved by viral transduction, limiting the ability to regulate dose or region, and bringing significant hurdles.

(6.) Brain delivery of RNAi therapies. siRNA therapeutics in the CNS offer significant challenges for delivery—methods have included the use of naked RNA duplexes[12], chemically modified duplexes for stabilization in vivo, peptides for trans-membrane delivery[1,13], as well as cholesterol modification or lipid modifications; liposomal carriers and other nanoparticles have also been used[14]. Specific ligands such as short peptides derived from the Rabiesvirus coat glycoprotein (RVG), can bind to nicotinic receptors on neurons, and thus target siRNAs to neuronal membranes[13]. The RVG has been linked to a short polyarginine stretch (RVG-9R), which then can noncovalently but stably associate with RNA; the polyarginine also is well described to enable transmembrane transduction of macromolecules. In addition to neuronal targeting and transduction, the RVG-9R peptide appears to stabilize the RNA species[13]. siRNA-RVG have been reported to work by peripheral administration, but this poses many challenges, as it requires large amounts of material, and increases the risk for immune response[14]. The invention provides smiRNAs associated with RVG-9R and their use for direct intracerebral delivery by injection. In contrast to siRNA therapies, miRNA delivery has primarily been pursued using viral vectors in the CNS, such as AAV2[8].

Figure 2:
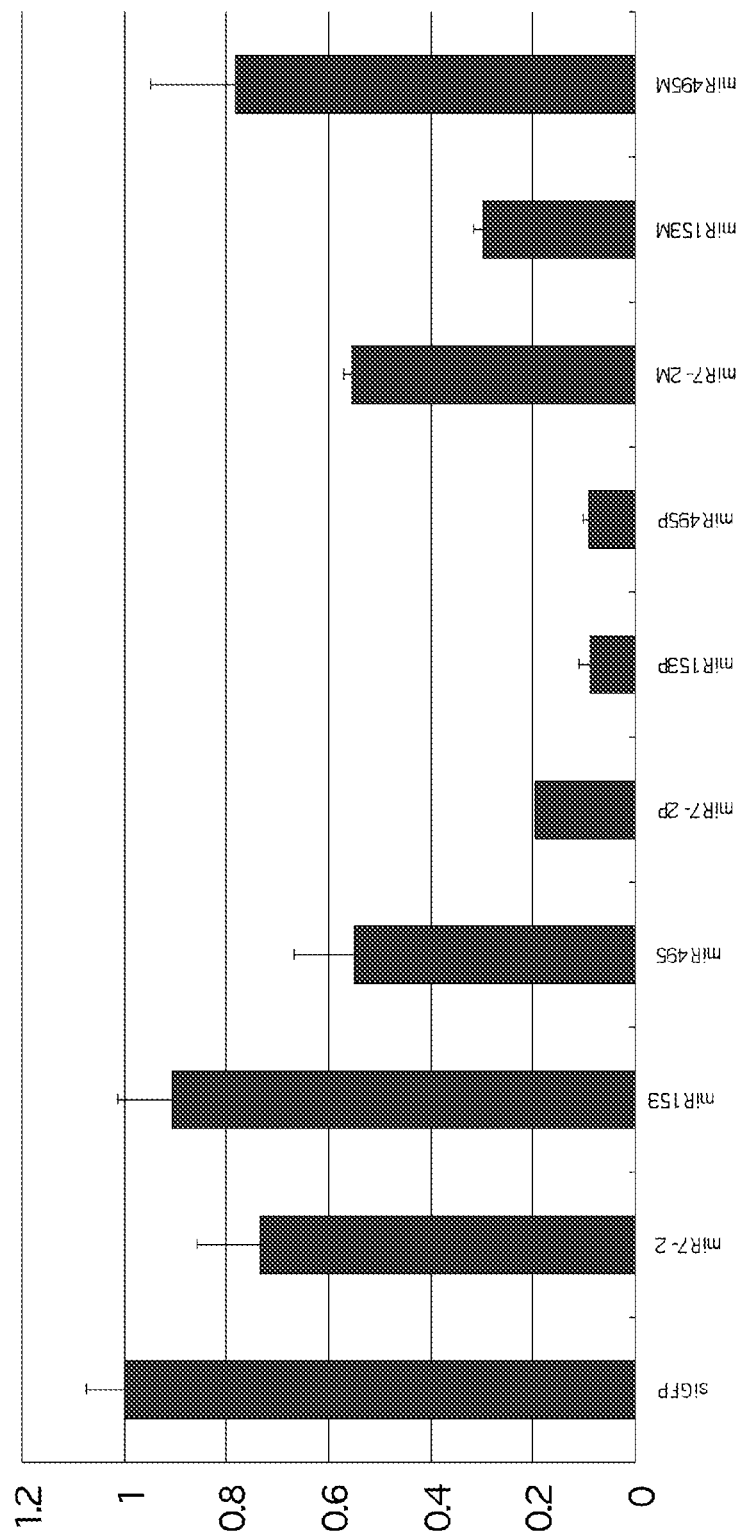
FIG. 2 shows luciferase assays conducted in HEK293 cells with a reporter that harbors a 1.2 kb 3'UTR aSyn region; values are presented as ratios to Renilla control reporter[1]. Co-transfection of plasmids that harbor indicated miRNA, 'optimized' to perfectly complement the aSynuclein target site (with 'M' (single strand modified miR-153-SNCA)), or optimized at both miR and miR* strands (with 'P' (double strand modified miR-153-SNCA)) to remove the miRNA bulge (as seen in FIG. 1 in the endogenous miRNA-153). N=6/group; p<0.001 for smiR-153P vs. miRNA species. siGFP is a negative control sequence.

Current Stage of Development:

1. Endogenous miRNAs that target aSynuclein. In our studies and other studies[15,16], a number of miRNAs have been identified which play roles in the regulation of aSyn (FIG. 2). Such miRNAs would potentially be advantageous as therapeutics, over artificial siRNA constructs, based on safety concerns and as detailed above. However, limitations exist. First, miRNAs display significantly lower specificity (because of multiple targets) and less potency than siRNAs. Second, viral delivery systems typically used for miRNA are more difficult to dose precisely, and present significant regulatory hurdles.

2. 'Perfecting' endogenous miRNAs. To address the first issue, we used an alternative approach, where we perfected complementarity of the relevant endogenous miRNAs (for example but not limited to miR-153 and miR-7) to achieve maximum binding to aSynuclein 3'UTR); specificity was confirmed by computational BLAST search. This led to improved potency in vitro (FIG. 2). In certain embodiments, miRNAs may be optimized by also incorporating the changes into the second strand of the miRNA loop, thus leading to a loss of the miRNA 'bulges' (see FIG. 1A).

3. Preparation of smiRNA for delivery. Delivery of naked double-stranded siRNAs into the CNS has been reported[17]. miRNA precursors are typically 50-150 base long single stranded with complex tertiary structure, and harbor stem-loop structures that contain the mature sequences (FIG. 1). These could be efficiently synthesized in vitro by T7 polymerase up to 120 ug in a 20 ul reaction). Briefly, we synthesize a single-stranded DNA oligonucleotide that is complementary to the miRNA precursor (IDT Bio), with a T7 promoter sequence at its 3' terminus. In vitro Klenow fill-in and T7 transcription is then performed using a standard kit (Epicentre Tech, as per instructions). The smiRNA is then treated with DNAse and dephosphorylated by calf intestinal phosphatase, followed by gel purification, HPLC, and desalting[17]. Product is verified by MALDI-TOF mass spectrometry, and the presence of endotoxin is assayed. Up to 100 ug can be purified from an initial 20 ul reaction, and thus the procedure is quite robust. Results presented herein and a prior report indicate that injection of such products does not induce an interferon response[17]. See Gondai et al., the contents of which is hereby incorporated by reference in its entirety.

Figure 3:
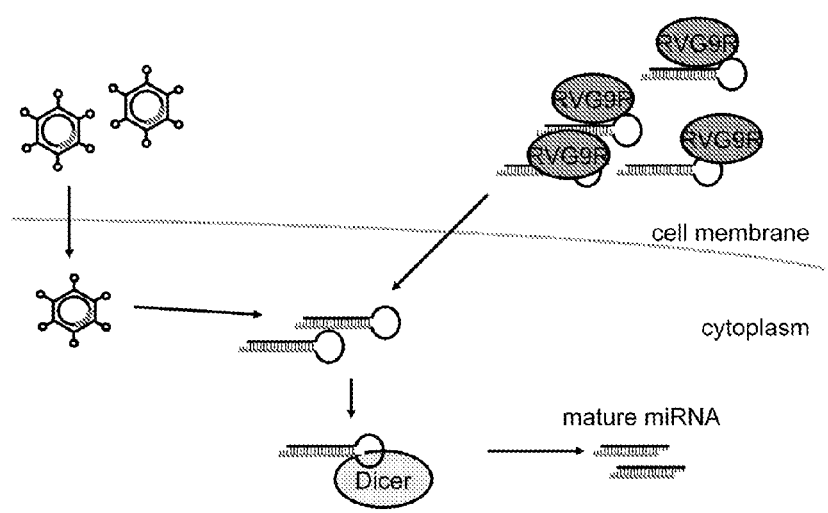
FIG. 3. Viral vectors are typically used to encode miRNA for delivery (left side of figure). We have instead generated novel synthetic optimized smiRNA; these are delivered using an RVG-9R peptide that allows for neuronal targeting, cell transduction, and stabilization (right side of figure).

4. Delivery method. We sought a non-viral approach for delivery (FIG. 3), and our preliminary studies indicate that smiRNA delivery is efficient when conjugated with peptide RVG-9R. Prior publication suggested that RVG-9R complexed with siRNAs could be peripherally administered[13], but that requires large amounts of material, and also would more likely lead to untoward effects such as immune activation relatively to intracerebral.

Figure 4:
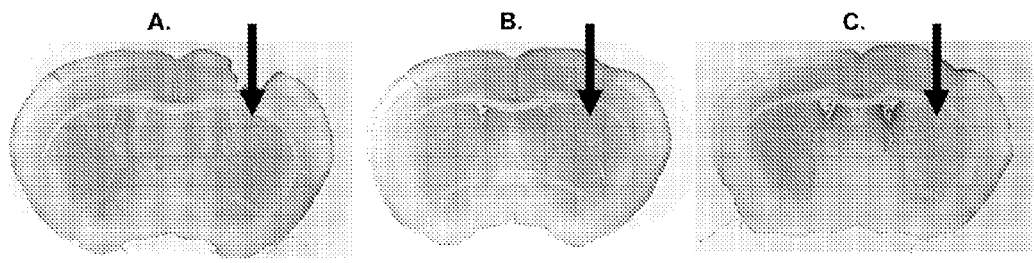
FIGS. 4A-C show 10-mo old PAC male mice were infused in the striatum for 10 weeks at arrow with (A) siGFP/RVG9R, (B) miR-153//RVG9R, or (C) smiR-153/RVG9R. Infusion of only the latter leads to a dramatic reduction in aSyn accumulation (n=3).

To test efficacy in vivo on human aSyn: we used PAC (P1 artificial chromosome) aSyn transgenic mice (10-mo old heterozygous male[18]) that overexpresses human wild-type a-Syn that includes the 3'UTR. Human aSyn expression is easily detected by IHC with a human-specific antibody (LB-509; FIG. 4). Osmotic minipumps (Alzet 1007D) are filled with siRNA solution containing 21.6 ug smiRNA-153 (0.5 nmoles, mixed with 5 nmoles RVG-9R; 6 ul per day over 14 days) in aCSF (Harvard Apparatus) and primed as per the manufacturer's instructions. Stereotaxic surgical implantation of a 3.00 mm cannula at 0 mm posterior and 2.5 mm lateral from bregma and 2.5 mm deep targets the right striatum, is essentially as described[19,20] and as per the manufacturer's instructions (see also our prior publication, albeit in rat[21]). All anesthesia and surgical techniques are strictly as per the CUMC IACUC. After 14 days, mice are sacrificed for standard immunohistochemical analysis of the brain.

These analyses revealed a dramatic reduction of aSynuclein immunoreactivity throughout the striatum (approximately 70%; n=3), and extending to the cerebral cortex (FIG. 4), by a smiRNA-153/RVG-9R conjugate Importantly, transduction of EGFP miRNA/RVG-9R, or of non-optimized miR-153/RVG-9R, were ineffective. No pathological evidence of inflammation was apparent on gross pathology, and animals did not display obvious behavioral or other abnormalities with any of these treatments.

Further Characterization and Optimization of smiRNA In Vivo.

Our initial studies show that optimized miRNAs, for example but not limited to smiRNA-153 (SNCA), offer high specificity, potency, and can be effectively delivered.

smiRNA species. We will first extend the in vivo analysis as above for miR-153/RVG-9R to mir-7/RVG-9R and miR-495/RVG-9R, or any other suitable miRNA or optimized variant thereof (with siGFP/RVG-9R as a control sequence). All studies in this subsection are in the context of unilateral injection of human SNCA PAC mice as above[18,22] (n=6 animals per group, based on preliminary data and reported variability[19,20]) Analysis will initially be by IHC as above, for human aSyn, and pathological examination by Nissl staining for florid astrocytosis or microglial infiltration. Control EGFP will be included as a group. An additional identical set of animals will be examined by Western blotting for aSynuclein using the LB-509 antibody of brain extracts from striatum, midbrain, cerebral cortex, cerebellum, and hippocampus (48 animals total). IHC and Western blot quantification of aSyn is performed using NIH Image software.

Dosing. We will perform a dose-response curve with one of the above 3 chosen smiRNAs, or any combination thereof, based on efficacy, including the current dose (0.5 nmoles); and 0.2, 1, 3, 10, and 20 nmoles/mouse. Our intention is to determine both the peak efficacy, in terms of reduced aSyn immunohistochemistry, and the maximum tolerated dose. Analysis is as above; animals are also monitored daily for weight, grooming, and general activity in cage. To be considered as efficient and selected for further development, a given miRNAs should lead to a reduction of aSyn superior to 50% when compared to control randomized miRNAs throughout the striatum; our initial data meet this. This threshold has been chosen considering that in familial form of Parkinsonism induced by a aSyn gene duplication, the level of aSyn is at least 50% superior to the normal one and causes a PD phenotype (36 animals will be used here).

Preliminary kinetics. To further determine pharmcokinetics, analysis of aSyn expression will be analyzed by IHC at 3 days, 7 days, as well as 14 days after dosing. In additional animals, pumps will be removed at 14 days, and analysis performed at a subsequent 1-week, 2 weeks, and 4 weeks. An identical set of animals will be prepared, but analyzed by Taqman assay (ABI) specific for the smiRNA chosen as in 1.1, performed on RNA preparations from striatal tissue as well as cerebral cortex, cerebellum and hippocampus. In parallel, we will also perform TaqMan (ABI) analysis by rtPCR of aSynuclein mRNA accumulation; this will inform us as to whether the smiRNA lead to degradation of aSyn mRNA or only reduce translation; and inform on half-life of RNA and protein species. (48 animals total).

Analysis and quantification of kinetics of the smiRNA, here performed by TaqMan analysis, will allow for correlation of accumulation with potency. Additional approaches, such as fluorescent labelling of the smiRNA, can be used as well, but would not clearly distinguish full-length smiRNA from degradation products. We do not here include peripheral administration of these leads (given the caveats above), but future studies may include this. If potency appears insufficient, we will consider a combinatorial approach as well. A potential issue is that aSyn may include shorter 3'UTR that do not include all targets; however our preliminary data and published studies are supportive of the approach[15,16].

Evaluation of Toxicity, Inflammation, and Specificity of the smiRNA Lead Therapeutic.

Our initial studies indicate potency without a frank inflammatory response. Additional studies may be performed, using further analyses, and at later time points. Studies in this section will use the appropriate animals including where necessary aSyn KO mice below.

Immunohistochemical analysis for toxicity and neuronal loss. For evaluation for neuron loss, we will use standard analyses to validate striatal morphology and symmetry with the control side; antibodies include DARPP-32. Dopamine neuron number in the SN, as well as neuronal processes to the striatum, will be quantified as described[2,23]. We will evaluate most closely the region nearest to the injection site, and within concentric circles, using NIH Image software. Additional evidence for toxicity will be assayed by activated Caspase 3 and TUNEL staining[23].

Neurochemistry. We will quantify dopamine and serotonin content in striatal tissue and midbrain as described[2,23].

Inflammatory response. We will quantify for evidence of microglial activation (Iba-1, as well as astrogliosis (GFAP), either at 2 weeks after implantation, or 6 weeks later. Accumulation of inflammatory cytokines, as well as evidence for an immune response to RVG-9R peptide, will be assessed by ELISA as described[13]. Interferon-α levels will be quantified by ELISA, although prior studies have found no evidence for such a response with similar T7 products[17].

Target specificity. To further quantify evidence of off-target or inflammatory responses, we will evaluate expression of a series of other neuronal, synaptic-vesicle related proteins in by IHC and Western blotting of striatal tissue extracts; of particular interest are those neuronal mRNAs computationally predicted to be normally targeted by a given non-perfected miRNA (by TargetScan, MIT): eg, for miR-153 includes APP, A2BP1, and VAMP2; for miR-7 includes BACE1, Shank3, and Synapsin2. We will also quantify other synaptic proteins such as Synaptobrevin2 and VMAT2. Any changes may be secondary to the reduced aSyn protein (transgenic human aSyn or endogenous mouse, with only 4 nucleotides different at the 3'UTR miR-153 target).

Our data have not revealed evidence for significant inflammation. If we observe evidence for inflammation, additional purification may be helpful; additional liposomal membranes may be preventative[24]. If we see alterations in non-aSyn synaptic proteins, we may perform an additional set of injections into aSyn knockout mice and controls[2]. Off-target effects of smiRNA should still be observed in KO mice; effects secondary to aSyn reduction should not. A more global approach would be to use gene expression array analysis on striatal tissue; we will consider this additional approach.

Behavioral Rescue of A53T PAC Transgenic Mice

Our objective here is to show efficacy in a mouse model of aSyn pathology. We choose to focus on an additional PAC transgenic animal aSynuclein mouse, but harboring an A53T allele. This animal shows a 50% reduction in ambulatory activity at 6 months of age, as well as other activity changes[18,22].

We will perform bilateral intrastriatal injections of smiRNA, otherwise as above. Animals will be treated for 1 month, from 5 months of age, and then analyzed at 6 months of age precisely as described for altered open-field locomotion[18]. 25 animals will be prepared in each group. Subsequently, we will validate transgene aSyn knockdown by IHC as above. (50 animals total for this component; an additional time point may be added [3 months treatment from 3 months of age] if initial studies do not show clear efficacy), but otherwise identical.

We will focus on the mild behavioral findings in the PAC mice, as these are targeted by our leads, and given that they do recapitulate aspects of PD pathology. A limitation here is that we focus on striatal canulla placement, but have not yet clearly validated the extent; thus if midbrain aSyn knockdown is needed to suppress the phenotype, it may be necessary to alter canulla placement. Similarly, longer time course may be needed; 1 month is the most we can achieve without replacing the pumps; that may be necessary. We could also use an MPTP assay, as we and others report that aSyn loss is protective, this would require efficacy at the endogenous murine aSyn locus, which will be evaluated; such an MPTP study would be valuable, but require additional resources. A particularly interesting aspect of the A53 PAC mice is their enteric phenotype, which we would be eager to pursue with systemic treatment.

The studies described herein can be extended to safety studies on biologicals, including in monkey, as well as GMP production. In the context of larger brains, a key issue will be the extent of diffusion (especially to the Substantia Nigra), and thus how canulae are placed.

REFERENCES FOR EXAMPLE 1

1. Kim, J., et al. A MicroRNA feedback circuit in midbrain dopamine neurons. *Science* 317, 1220-1224 (2007).

2. Abeliovich, A., et al. Mice lacking alpha-synuclein display functional deficits in the nigrostriatal dopamine system. *Neuron* 25, 239-252 (2000).
3. Dauer, W., et al. Resistance of alpha-synuclein null mice to the parkinsonian neurotoxin MPTP. *Proc Natl Acad Sci USA* 99, 14524-14529 (2002).
4. Klivenyi, P., et al. Mice lacking alpha-synuclein are resistant to mitochondrial toxins. *Neurobiol Dis* 21, 541-548 (2006).
5. Gorbatyuk, O. S., et al. In Vivo RNAi-Mediated alpha-Synuclein Silencing Induces Nigrostriatal Degeneration. *Mol. Ther.*
6. Bartel, D. P. MicroRNAs: genomics, biogenesis, mechanism, and function. *Cell* 116, 281-297 (2004).
7. Saba, R. & Schratt, G. M. MicroRNAs in neuronal development, function and dysfunction. *Brain Res* 1338, 3-13.
8. Davidson, B. L. & Boudreau, R. L. RNA interference: a tool for querying nervous system function and an emerging therapy. *Neuron* 53, 781-788 (2007).
9. Su, H., Trombly, M. I., Chen, J. & Wang, X. Essential and overlapping functions for mammalian Argonautes in microRNA silencing. *Genes Dev* 23, 304-317 (2009).
10. Grimm, D., et al. Fatality in mice due to oversaturation of cellular microRNA/short hairpin RNA pathways. *Nature* 441, 537-541 (2006).
11. McBride, J. L., et al. Artificial miRNAs mitigate shRNA-mediated toxicity in the brain: implications for the therapeutic development of RNAi. *Proc Natl Acad Sci USA* 105, 5868-5873 (2008).
12. Lewis, J., et al. In vivo silencing of alpha-synuclein using naked siRNA. *Mol Neurodegener* 3, 19 (2008).
13. Kumar, P., et al. Transvascular delivery of small interfering RNA to the central nervous system. *Nature* 448, 39-43 (2007).
14. Nguyen, T., Menocal, E. M., Harborth, J. & Fruehauf, J. H. RNAi therapeutics: an update on delivery. *Curr Opin Mol Ther* 10, 158-167 (2008).
15. Doxakis, E. Post-transcriptional regulation of alpha-synuclein expression by mir-7 and mir-153. *J Biol Chem* 285, 12726-12734.
16. Junn, E., et al. Repression of alpha-synuclein expression and toxicity by microRNA-7. *Proc Natl Acad Sci USA* 106, 13052-13057 (2009).
17. Gondai, T., Yamaguchi, K., Miyano-Kurosaki, N., Habu, Y. & Takaku, H. Short-hairpin RNAs synthesized by T7 phage polymerase do not induce interferon. *Nucleic Acids Res* 36, e18 (2008).
18. Kuo, Y. M., et al. Extensive enteric nervous system abnormalities in mice transgenic for artificial chromosomes containing Parkinson disease-associated alpha-synuclein gene mutations precede central nervous system changes. *Hum Mol Genet.* 19, 1633-1650.
19. Thakker, D. R., et al. Neurochemical and behavioral consequences of widespread gene knockdown in the adult mouse brain by using nonviral RNA interference. *Proc Natl Acad Sci USA* 101, 17270-17275 (2004).
20. Thakker, D. R., et al. siRNA-mediated knockdown of the serotonin transporter in the adult mouse brain. *Mol Psychiatry* 10, 782-789, 714 (2005).
21. Yamashita, T., et al. Dissociation and protection of the neurovascular unit after thrombolysis and reperfusion in ischemic rat brain. *J Cereb Blood Flow Metab* 29, 715-725 (2009).
22. Gispert, S., et al. Transgenic mice expressing mutant A53T human alpha-synuclein show neuronal dysfunction in the absence of aggregate formation. *Mol Cell Neurosci* 24, 419-429 (2003).
23. Macleod, D., et al. The Familial Parkinsonism Gene LRRK2 Regulates Neurite Process Morphology. *Neuron* 52, 587-593 (2006).
24. Pulford, B., et al. Liposome-siRNA-peptide complexes cross the blood-brain barrier and significantly decrease PrP on neuronal cells and PrP in infected cell cultures. *PLoS One* 5, e11085.

Example 2

Therapeutic Description: Generation of novel miRNA precursor-based gene therapies that target aSynuclein expression in midbrain dopamine neurons. It is postulated that the accumulation of α-Synuclein protein participates in 'sporadic' PD pathology, and that aSyn accumulation is endogenously regulated at a post-transcriptional level by microRNAs in dopaminergic neurons.

MicroRNAs (miRNAs) are evolutionarily conserved, non-protein coding transcripts that play an important function in post-transcriptional regulation of gene expression. Mature miRNAs, 18-25 nucleotides long, are processed from 200-300 nucleotide-long primary (precursor) transcripts by the Drosha and Dicer endonuclease complexes, consecutively. Mature miRNAs guide the cleavage of target mRNAs and/or inhibits their translation (He and Hannon, 2004). First characterized in invertebrates, several hundred miRNAs have been identified in vertebrates, but only a few of them have been associated with specific cellular functions. miRNAs have been identified that are expressed during differentiation to a neuronal phenotype and to control neuronal identity establishment, either in vivo (Johnston et al., 2005), in vitro (Conaco et al., 2006) or in the context of ES cell cultures (Kawasaki et al., 2003), or that regulates neuronal morphogenesis in response to extrinsic trophic signals (Vo et al., 2005) or dendritic spine development (Schratt et al., 2006). More recently it was shown that miRNAs are needed for dopaminergic neurons maintenance in brain (Kim et al., 2007).

RNA interference has been increasingly used for several years to reduce the expression of targeted genes in a wide range of tissues and cells, by using synthetical short interfering RNA (siRNA) or short hairpin RNA (shRNA) coded by an expression cassette. In ceratin embodiments, the invention provides methods of using miRNA to reduce the expression of aSyn. There are at least 2 major advantages to the use of miRNAs, rather than artificial siRNAs or shRNAs, for gene silencing in vivo. First, miRNAs are part of an endogenous gene regulation process. This means that the sites targeted by miRNAs on mRNAs are likely to have a tertiary structure permitting the access of regulatory elements (miRNA+proteins complexes), which is a crucial criterion for the efficiency of gene silencing through RNAi mechanisms. Second, the use of an endogenous existing mechanism of gene regulation (in contrast with exogenous siRNAs or shRNAs) is likely to be better tolerated by the cells and to generate less side effects. In a recent animal model study, the high levels of shRNA expression needed to achieve efficient silencing were indeed shown to be toxic in liver and lethal, due to saturation of the endogeneous siRNA pathway (Grimm et al. 2006).

Figure 5:
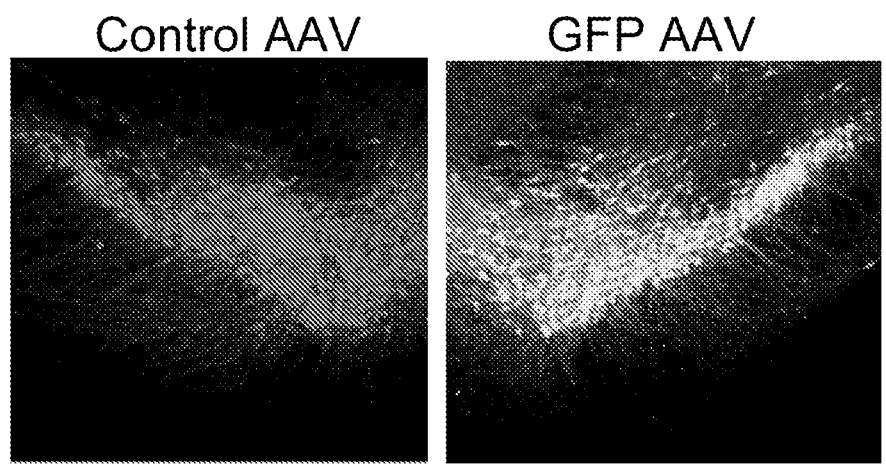
FIG. 5 shows AAV2 vector transduction of 8 week old C57BL6/j mouse SN. See technical stereotaxy details in text, other methods as in MacLeod et al., (2006).
Figure 6:
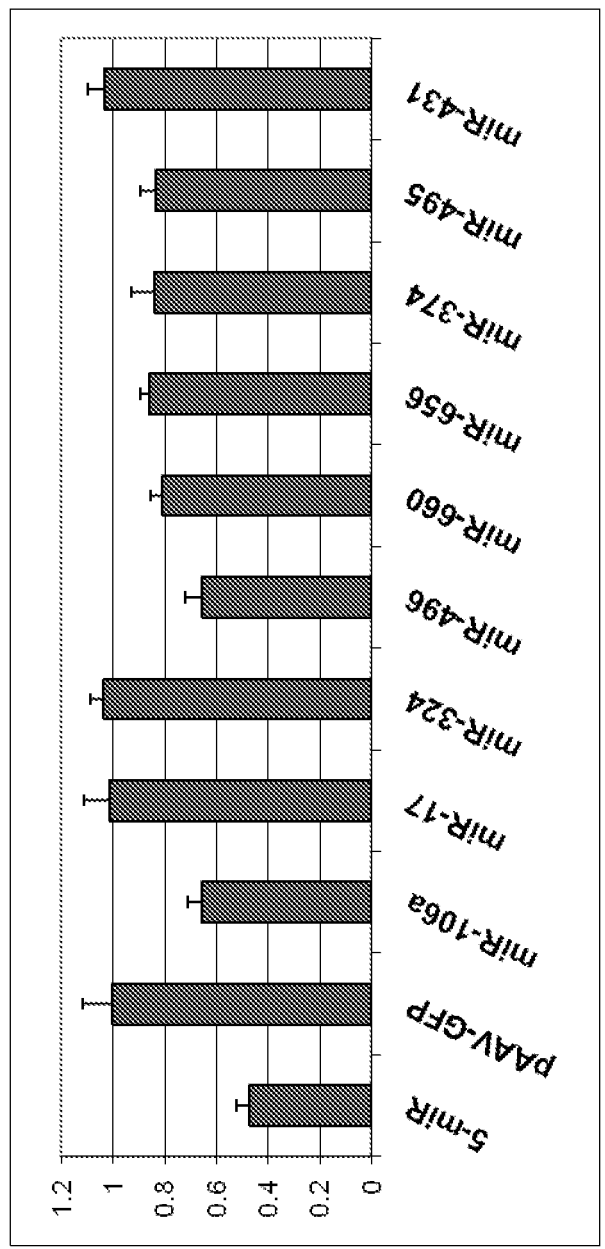
FIG. 6 shows effect of miRNAs on expression levels in a luciferase assay, which uses a luciferase transgene with the 3'UTR of APP. Normalized luciferase activity for a (Luc)+ (APP 3'UTR) transgene cotransfected in COS cells with different miRs or control: 5-miR: pAAV-GFP plasmid including a concatenation of microRNA cassettes coding for microRNA-106a,17, 324, 101 and 381 pAAV-GFP: Negative control (no microRNA coded) miR-X: pAAV-GFP plasmid including a of microRNA cassette coding for microRNA-X.
Figure 7:
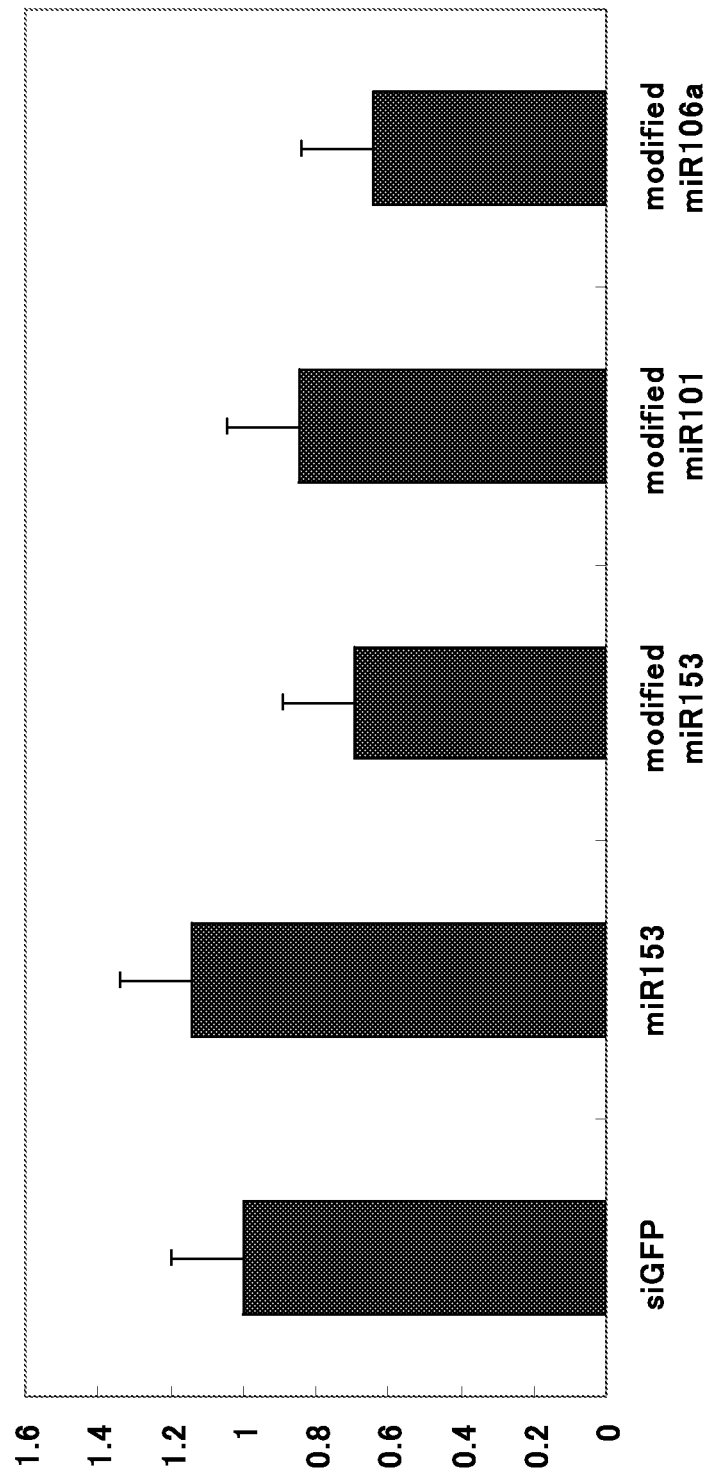
FIG. 7 shows in vitro data in HEK293 tissue culture cells transfected with a luciferase assay vector that harbors a 3'UTR from the human APP gene, to reflect regulation of the APP gene by miRNAs, modified miRNAs and controls. This experiment used the synthetic T7-generated miRNAs (10 nM), as described herein, that target 3'UTR of APP. Compared to a control, there is no significant effect of the endogenous miR-153. The modified miR153, modified to be perfectly complementary to the APP 3'UTR sequences, has effect in the luciferase assay. There is also effect with the perfected version of miR-106 (perfected on both strands).
Figure 8:
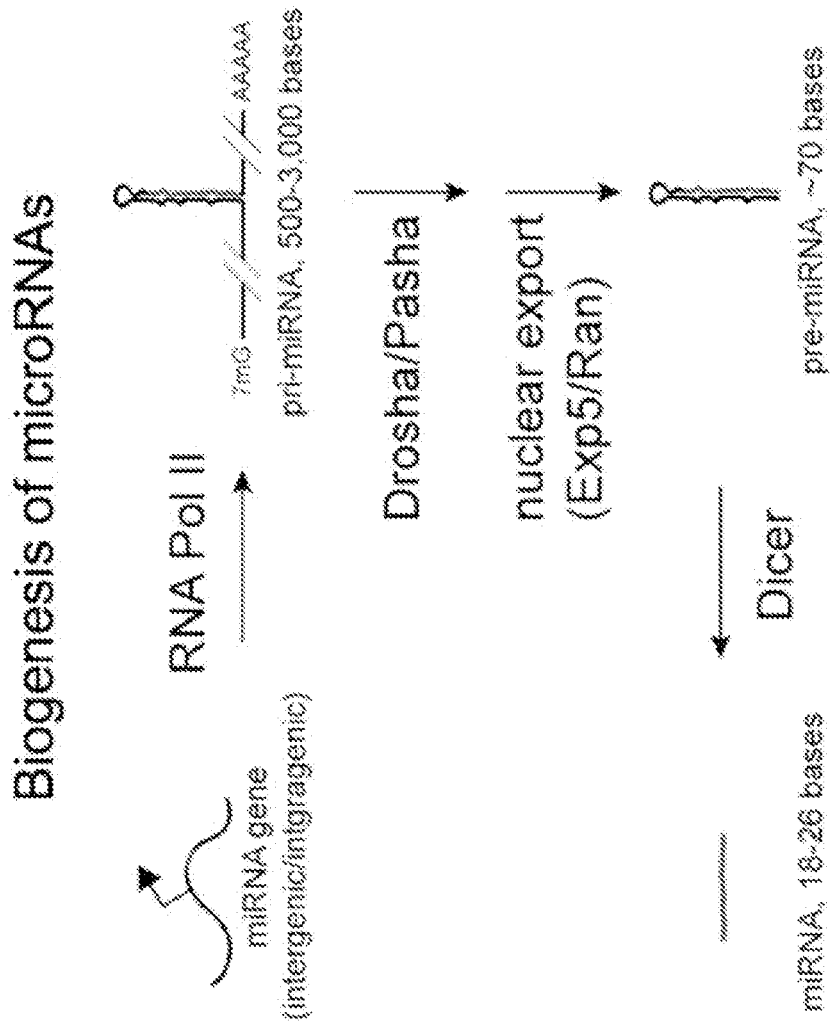
FIG. 8 shows: natural miRNA biogenesis.
Figure 9:
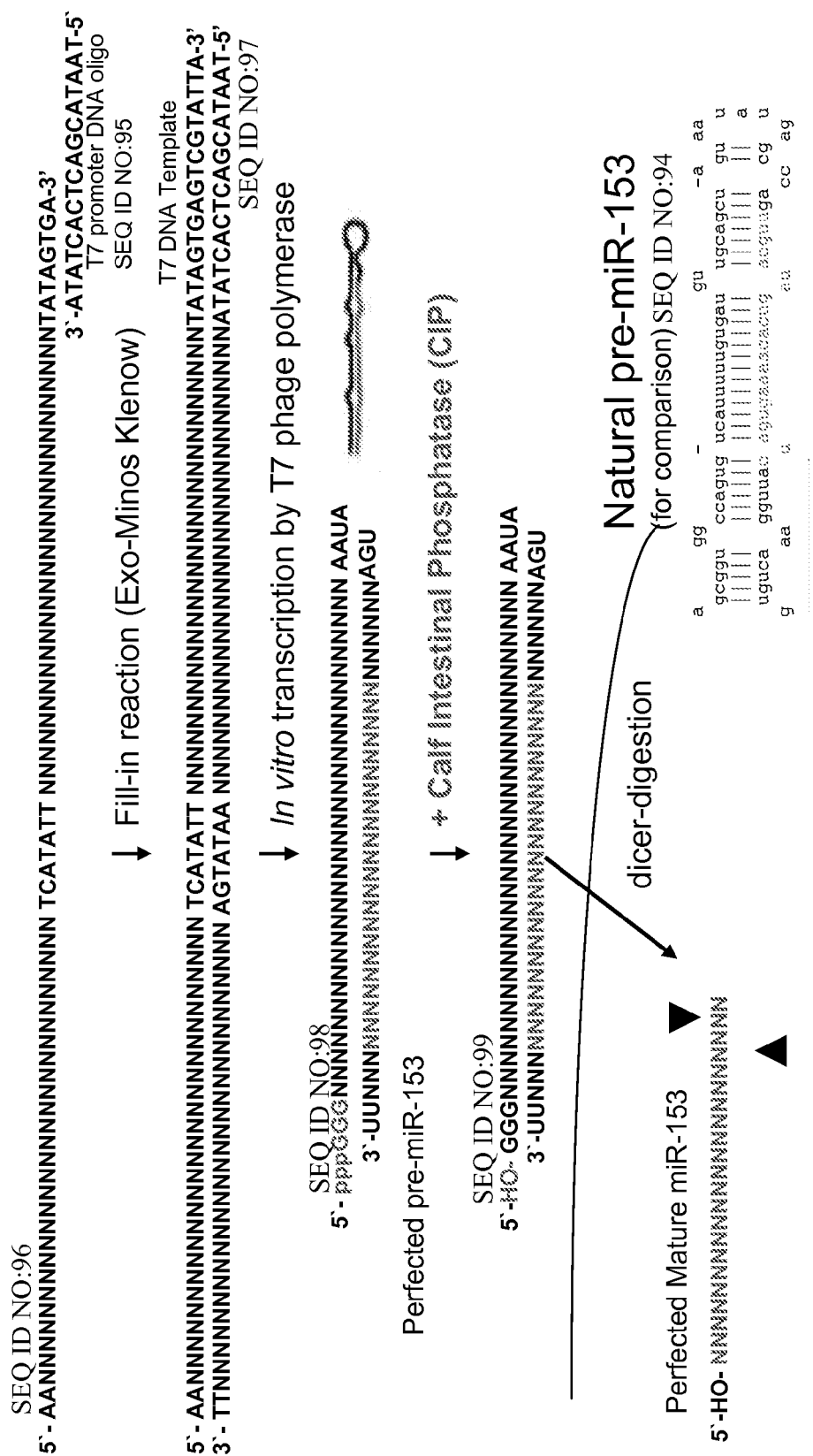
FIG. 9 shows one embodiment of a method to make perfected miRNA by synthesis in vitro. SEQ ID NO: 94 is the sequence of natural pre-miR-153 as depicted in FIG. 9. SEQ ID NO: 95 is the sequence of T7 DNA promoter oligo as depicted in FIG. 9.

In certain aspects, the invention provides generation and use of therapeutics for continued or chronic treatment. Given the apparent potential toxicity of chronic siRNA approaches in vivo, the use of miRNA-based therapies provides certain advantages and benefits. For example, a recent study shows that the use of shRNA expressed by AAV vectors in brain was shown to exhibit toxicity, this toxicity being abolished when the same vectors were used to silence the same genes by using a miRNA expression cassette (McBride et al. 2008). Thus, the use of microRNA, including but not limited to the modified miRNAs of the invention, is a promising strategy to reduce aSyn expression and accumulation that is more likely to be useful as a clinical therapy than the artificial shRNAs (Sapru et al., 2006) or ribozymes (Hayashita-Kinoh, 2006). Viral transduction with a control AAV2-GFP vector effectively and reproducibly transduces 70-90% of midbrain dopaminergic neurons (FIG. 5).

Identification of miRNAs predicted to regulate aSyn that are expressed in midbrain in humans. See Table 1.

miRNAs that are likely to participate in post-transcriptional regulation of alpha-synuclein expression were predicted using TargetScan (Whitehead Institute, (Lewis, 2003)), miRBase Targets (Sanger Institute, (Griffiths-Jones, 2006)) and miRanda (Memorial Sloan-Kettering Cancer Center, (John, 2004)) based on both the complementarity of their mature sequence with parts of the 3' UTR of alpha-synuclein mRNA and their conservation between species.

As the miRNAs that regulate alpha-synuclein should be expressed in the same cell types, the midbrain expression of miRNAs is a necessary prerequisite for a miRNA to regulate alpha-synuclein expression in dopaminergic neurons.

Among the candidate miRNAs found for alpha-synuclein regulation, eight (miR-16, miR-93, miR-101, miR-106, miR-148, miR-324-3p, miR-338-3p, miR-374) are especially interesting, as we found their precursors to be downregulated in midbrains of PD patients in comparison to control midbrains (Kim, 2007; see Table 1). We may hypothesize that these microRNAs are expressed in midbrain dopaminergic neurons and that the decrease observed in PD samples is a consequence of the loss of this cell population during PD progression. We thus have experimental evidence that the miRNAs from those two groups are expressed in midbrain, which make them good candidates to test for alpha-synuclein regulation.

Identification of microRNAs that regulate aSyn levels in human ES cells-derived cultures of dopaminergic neurons.

The miRNAs predicted to target human aSyn expression that were shown to be expressed in midbrain (see Table 1) will be screened for regulation of aSyn protein accumulation. Rather than using artificial systems with reporter genes, which may lead to false results, the regulation of endogenous human aSyn expression will be evaluated in human ES-derived dopaminergic neuron cells, to be the closest possible to the therapeutical context.

Selecting miRNAs or miRNAs tandem that reduce aSyn in dopaminergic neurons in vitro.

ES-derived neuron cultures (at the early maturation stage (Stage 5, day 1; Kim et al., 2007) will be transduced in triplicates by AAV2 vectors (1 ul of $10^{12}$ IU/ml) expressing either a candidate primary (200-300 bp precursor) microRNA or control microRNA with an equivalent structure but in which the mature sequence involved in target recognition, will be randomized. The primary microRNA will be inserted in an artificial intron upstream of a GFP coding sequence, under the control of the CMV promoter. The primary miRNA will thus be a part of the immature GFP transcript and will be processed after the splicing by the endogeneous miRNA machinery, thus further mimicking the natural process of miRNA production, as most of miRNAs were shown to come from intronic sequence (Du et al., 2006) (Kim and Kim 2007). Using this approach, 8 miRNAs will be evaluated out of the 13 predicted to target aSyn and that we showed to be expressed in human midbrain.

The readout taken into account for the efficiency of the different miRNAs will be the ability to reduce the protein level of aSyn as measured by Western-Blot (normalized to beta-actin accumulation by Western blot), when compared to the aSyn level in cells transduced by the randomized control miRNA. To be considered as efficient and selected for further development, a given miRNAs should lead to a reduction of aSyn superior to 50% when compared to control randomized miRNAs. This threshold has been chosen considering that in familial form of Parkinsonism induced by aSyn gene duplication, the level of aSyn is at least 50% superior to the normal one and causes a PD phenotype. The reduction of this level by 50% would probably be enough to rescue this phenotype. This is further discussed below.

Identified miRNAs that exhibit a reduction of aSyn expression superior to 50%, the sequences of the microRNA will be further optimized: the relative efficacy of miRNAs at different targets is a consequence of sequence complementarity/homology between the target 3'UTR and the mature miRNA. All aSyn 3'UTR targets of miRNAs are imperfect and include mismatches which reduce efficacy. The modifications of miRNAs mature sequences towards a optimal match with the targeted sequence of aSyn is predicted to lead to an increase in specificity and efficiency, and thus to reduce off-target related toxicity. Specific sequence modifications are described herein.

A second approach will generate AAV vectors that include a tandem array of combinations of 2 or more of the most efficacious miRNA precursors in tandem. Such arrays of miRNAs are also naturally-occurring (He, L., et al., 2005), and there is substantial evidence for highly synergistic action of miRNAs. The small size (200-300 bp) of the primary miRNAs will furthermore enable the efficient concatenation of the miRNAs in a single AAV vector for a synergistic effect. In a non-limiting example, a total of 12 miRNAs combinations (resulting from the combinations between the 4 most effective miRNAs out of the 8 tested) will be tested using this approach.

The efficiency of the concatenation will again be evaluated by the ability of the constructs to reduce the protein level of aSyn as measured by Western-Blot in the ES-derived dopamine neurons. To be considered as efficient and selected for further development, a given miRNAs tandem should lead to a reduction of aSyn superior to 50% when compared to control randomized miRNAs plus lead to a significantly higher level of aSyn reduction than either of the miRNAs used to build the tandem.

In certain aspects, the invention provides methods of screening, multimerization, and optimization, to generate reagents to reduce aSyn protein expression using the endogenous miRNA pathway.

If none of the 8 initially tested miRNAs, identified by expression in normal midbrain reaches the 50% efficiency threshold, combinations of the most efficacious miRNAs will be evaluated and optimized, to reach efficacy above 50%.

A potential concern is that miRNAs target multiple transcripts, and thus off-target effects will potentially lead to toxicity. Such toxicity will be observed for a given miRNA if transduction by a vector expressing this miRNA leads to cells loss when compared to transduction with control randomized miRNA. Cell loss will be evaluated for dopaminergic neurons and total neurons in culture as described precisely in our prior publication (Kim et al., 2006). The specificity of miRNAs for the aSyn 3'UTR target will be improved by modifying miRNAs mature sequences towards optimal complementarity match with the targeted sequence of aSyn.

Investigate the ability of an AAV vector expressing anti-aSyn miRNAs to reduce the endogenous expression of aSyn in vivo in mouse midbrain.

In certain aspects the invention provides that an AAV2 vector expressing the selected microRNAs is able to reduce the expression of aSyn in midbrain dopaminergic neurons in vivo, and in the endogenous human gene context. In certain aspects, the invention provides that miRNAs or miRNAs tandem that reduce aSyn expression in dopaminergic neurons in vitro to reduce endogeneous aSyn expression in dopaminergic neurons in vivo.

Human SNCA PAC mice will be used (Gispert et al., 2003), for their very specific feature of bearing the whole human-aSyn gene on an artificial chromosome. The microRNA expressed by the AAV vector will have been optimized for the human aSyn 3'UTR, for a therapeutic development. As the miRNAs identified target the 3'UTR of transcripts, other transgenic mice strains built to model PD, which overexpress the sole coding sequence of human aSyn, could not be used for the current miRNA-based strategy.

AAVs containing the GFP gene with an intron containing either the microRNAs against aSyn or control scramble miR-NAs expression cassette will be stereotaxically injected in the substantia nigra of human SNCA PAC mice at 2-3 months of age, one side being injected with the miRNA vector to be tested, and the other side with a control miRNA vector (2 doses: 1 ul of $10^{11}$ or $10^{12}$ IU/ml). 8-10 mice will be used for each treatment. Six experimental groups gatherings the different treatment will be used, to assess ASyn expression for two doses of AAV at time points of 4 weeks and 6 months after injection by immunohistofluorescence as described (MacLeod, 2006). The use of double labeling, with an antibody coupled to a red fluorophore; green for the infected cells, from the GFP gene expressed by the AAV will permit to look for an inverse correlation between aSyn expression and transgene expression, which would be the proof of efficiency of the treatment. Quantitation will be performed by confocal microscopy precisely as described (MacLeod et al., 2006). Quantitation will also be performed by Western blotting of midbrain extracts for both Triton X-100 soluble and insoluble fractions; Western blotting is performed as in SA1, extract preparation and fractionation of insoluble fraction is performed as in Shendelman et al. (2004). Controls include b-Actin and GFP Western blotting for total protein and for transduction, respectively.

As this model of transgenic mice do not show marked behavioral deficit and neuronal loss (Gispert et al., 2003), the aSyn level in substantia nigra will be considered as the only significant output of this experiment. A 50% reduction of aSyn expression in animals treated by anti-aSyn miRNAs vs animals treated by control miRNAs is considered as a success threshold for this experiment, thus proving the ability of the treatment to reduce aSyn expression in vivo in dopaminergic neurons at a level likely to have a therapeutic effect. This is chosen given that familial Parkinsonism due to gene triplication (leading to up to 2× higher generation) causes disease.

aSyn transgenic mice, including those here, do not show consistent loss of dopamine neurons and thus may not accurately model the disease phenotype; thus, a viral approach may be used. A potential concern is that miRNAs overexpression might be toxic in the brain. However, it has been shown that the expression of several miRNA using AAV2 vectors in mouse brain was not toxic (McBride et al. 2008), if toxicity is observed, it is likely to be due to the specific sequence of miRNA that has been used.

If aSyn level is poorly reduced and if the number of GFP-positive cells in substantia nigra is consistent with an efficient transduction, then one possibility is that the murine endogeneous miRNA corresponding to the one expressed by the AAV2 vectors is already very high in dopaminergic neurons and that in consequence its increased expression would not lead to a strong reduction of aSyn expression. In that case, the second most efficient miRNA construct may be used.

Evaluation of the therapeutic effect of AAV vectors expressing anti-alpha synuclein miRNAs in a rat model of PD. Use of AAV2 vectors expressing anti-aSyn miRNAs may reduce the expression of aSyn and lead to rescue dopaminergic neurons in a rat model of PD based on the overexpression of aSyn.

miRNAs or miRNAs tandem reduce aSyn expression in dopaminergic neurons in vitro to rescue neurons in vivo in a model of PD induced by exogenous aSyn overexpression in dopaminergic neurons. Rat models of PD based on AAV-mediated midbrain neuron overexpression of human aSyn will be used as described (Kirik et al., 2002). This model has the advantage of producing a rapid degeneration of nigrostriatal neurons, which has not been consistently seen using transgenic expression approaches in animals (Kirik and Bjorklund, 2003). The wild type and mutated A53T version of human aSyn, responsible for a familial form of PD, lead to equivalent pathologic features in the rat model. In certain embodiments, the focus is on the wild-type model, and in treating sporadic forms of PD. The efficient transduction of midbrain dopamine neurons in adult rats is previously described (MacLeod et al., 2006). The size of aSyn cDNA (1.5 kb) permits to use a single AAV vector for both human aSyn and therapeutic miRNA expressions, which should considerably decrease the experimental variability. Four vectors will be built, resulting from the combination of wild-type human aSyn with anti-synuclein miRNA vectors, including a control scrambled miRNA precursors.

AAV vectors (2 doses: 1 ul of $10^{11}$ or $10^{12}$ IU/ml) will be stereotaxically injected in the substantia nigra of 3 months old anesthetized Sprague-Dawley rats (Kirik et al., 2002), one side being injected with an AAV2 vector expressing aSyn in tandem with the miRNA to be tested, and the other side with an AAV2 vector expressing Syn in tandem with a control miRNA. Based on previous studies, 8 rats will be used for each treatment and 2 doses of AAV2 will be used to generate different levels of infection. An experimental group will thus gather 8×2×3=48 rats. All analysis will be led 4 months after the infection, as in this model, aSyn expression was found to reach its maximum 8 weeks after infection and to remain stable until 24 months after infection (Kirik et al., 2002). A first experimental group will be used to evaluate aSyn expression by immunohistochemistry as previously described in the injected side (MacLeod et al., 2008). Neuronal loss will be assessed by immunohistochemistry for TH within the midbrain and will be done precisely as previously described (Kim et al., 2006). Total dopamine will be directly quantified in nigra and striatum extracts from a second experimental group, prepared and processed by high performance liquid chromatography (HPLC) as we already described (Martinat et al., 2006). Prior to the above analyses, animals will be used for testing amphentamine mediated-locomotor behavior, as assessed by rotatory behavior as is standard in the field and as has been described in detail in rodents (Martinat et al., 2004).

As one way of measurement, the aSyn level in substantia nigra will be evaluated. Another way measurement will assess the protection of dopaminergic neurons, directly evaluated by the TH immunohistochemistry in midbrain followed by a TH-positive cells count (performed precisely as detailed, Kim et al., 2006), and indirectly evaluated by the measurement of dopamine level in nigra and striatum extracts. The neuronal count will be considered as the main criterion to assess the success of the experiment. Being given that a the loss of up to 50% of DN may be compensated and thus lead to only minor phenotypes, a reduction by 50% of the DN loss in this model would be consider a threshold to validate the treatment, as it should permit to stabilize patients. If aSyn expression is significantly reduced in substantia nigra treated by specific miRNAs but no neuronal rescue is observed, one may hypothesized that the expression level of aSyn is still elevated enough to lead to DN death. In that case, the experiment should be done again with a lower viral load for the infection: this should lead to a lower aSyn overexpression, where reduction by microRNA will be more likely to rescue neurons.

These studies will optimize the miRNA precursor therapies and establish efficacy and preliminary safety. Subsequent studies will include primate MPTP models and the development of inducible expression.

REFERENCES FOR EXAMPLE 2

Abeliovich, A., et al., Mice lacking aSyn display functional deficits in the nigrostriatal dopamine system. Neuron, (2000) 25(1):p. 239-252.
Conaco, C., et al., Reciprocal actions of REST and a microRNA promote neuronal identity. Proc Natl Acad Sci USA, 2006. 103(7): p. 2422-7.
Gispert, S., et al., Transgenic mice expressing mutant A53T human aSyn show neuronal dysfunction in the absence of aggregate formation. Mol Cell Neurosci. 2003 24(2):p. 419-29.
Griffiths-Jones, S., et al., miRBase: microRNA sequences, targets and gene nomenclature. Nucleic Acids Res, 2006. 34(Database issue): p. D140-4.
Gründemann, J., et al., Elevated aSyn mRNA levels in individual UV-laser-microdissected dopaminergic substantia nigra neurons in idiopathic Parkinson's disease Nucleic Acids Res. 2008 36(7):e38
Hayashita-Kinoh, H., et al., Down-regulation of aSyn expression can rescue dopaminergic cells from cell death in the substantia nigra of Parkinson's disease rat model. Biochem Biophys Res Commun. 2006 341(4):p. 1088-95.
He, L. and G. J. Hannon, MicroRNAs: small RNAs with a big role in gene regulation. Nat Rev Genet, 2004. 5(7): p. 522-31.
He, L., et al., A microRNA polycistron as a potential human oncogene. Nature. 2005 435(7043): p. 828-33
John, B., et al., Human MicroRNA targets. PLoS Biol, 2004. 2(11): p. e363.
Johnston, R. J., Jr., et al., MicroRNAs acting in a double-negative feedback loop to control a neuronal cell fate decision. Proc Natl Acad Sci USA, 2005. 102(35): p. 12449-54.
Kawasaki, H. and K. Taira, Hes1 is a target of microRNA-23 during retinoic-acid-induced neuronal differentiation of NT2 cells. Nature, 2003. 423(6942): p. 838-42.
Kim, J., et al., A MicroRNA feedback circuit in midbrain dopamine neurons. Science, 2007. 317(5842): p. 1220-4.
Kirik, D. and Bjorklund, A., Modeling CNS neurodegeneration by overexpression of disease-causing proteins using viral vectors, Trends Neurosci. 26 (2003): p. 386-392.
Kirik, D., et al., Parkinson-Like Neurodegeneration Induced by Targeted Overexpression of Alpha—Synuclein in the Nigrostriatal System J. Neurosci. 2002, 22(7):p. 2780-91
Krichevsky, A. M., et al., Specific microRNAs modulate embryonic stem cell-derived neurogenesis. Stem Cells, 2006. 24(4): p. 857-64.
Lewis, B. P., et al., Prediction of mammalian microRNA targets. Cell, 2003. 115(7): p. 787-98.
MacLeod, D., et al., The familial Parkinsonism gene LRRK2 regulates neurite process morphology. Neuron. 2006 52(4):p. 587-93.
Martinat, C., et al., (2006). Cooperative transcription activation by Nurr1 and Pitx3 induces embryonic stem cell maturation to the midbrain dopamine neuron phenotype. Proc Natl Acad Sci USA 2008, 103(8):p. 2874-79.
Sapru, M K., et al., Silencing of human aSyn in vitro and in rat brain using lentiviral-mediated RNAi. Exp Neurol. 2006 198(2):p. 382-90.
Schratt, G. M., et al., A brain-specific microRNA regulates dendritic spine development. Nature, 2006. 439(7074): p. 283-9.
Shendelman, S., et al., DJ-1 is a redox-dependent molecular chaperone that inhibits alpha-synuclein aggregate formation. PLoS Biol. 2004 2(11):e362.
Singleton, A. B., et al., aSyn locus triplication causes Parkinson's disease. Science, 2003. 302(5646): p. 841.
Spillantini, M. G., et al., ASyn in Lewy bodies. Nature, 1997. 388(6645): p. 839-40.
Vo, N., et al., A cAMP-response element binding protein-induced microRNA regulates neuronal morphogenesis. Proc Natl Acad Sci USA, 2005. 102(45): p. 16426-31.

Example 3

Studies described in Examples 1 and 2, will be carried out to determine the effects of modified miRNAs of the invention directed to APP on the levels of APP. These studies include in vivo and animal models studies.

Further experiments on a rodent model can be carried out, as well as an analysis of potential side effects.

Future experiments include testing on higher mammals (eg. monkeys).

Examples of Sequences of the Invention

Example 4

Position 458-464 of SNCA 3' UTR 5'...UAUGUGAGCAUGAAACUAUGCAC...(SEQ ID NO: 1)

||||||| hsa-miR-153    3'   CUAGUGAAAACACUGAUACGUU (SEQ ID NO: 2)

hsa-miR-153-1 natural
Oligo;
(SEQ ID NO: 3)
5'-AAGGCTCACAGCTGCCAGT GTCATTTTTGTGATCTGCAG

CTAGTATTCTCACTCCAG TTGCATAGTCACAAAAGTGATC ATTGGCAG

GTGTGGCTATAGTGA-3'

Oligo is subjected to in vitro transcription (for
example but not limited to methods described
herein), CIP-treatment
Product;
(SEQ ID NO: 4)
5'-HO- GGGGGCUCACAGCUGCCAGU GUCAUUUUUGUGAUCUGCAG

CUAGUAUUCUCACUCCAG UUGCAUAGUCACAAAAGUGAUC

AUUGGCAGGUGUGGC UU-3' simiR153-1 ss-perfected
Oligo;
(SEQ ID NO: 5)
5'-AAGGCTCACAGCTGCCAGT TTGTGAGCATGAAACCTGCAC

CTAGTATTCTCACTCCAG GTGCATAGTTTCATGCTCACATA

ATTGGCAGGTGTGGCTATAGTGA-3'

Oligo is subjected to in vitro transcription (for
example but not limited to methods described
herein), CIP-treatment
Product;
(SEQ ID NO: 6)
5'-HO- GGGGGCUCACAGCUGCCAGU UUGUGAGCAUGAAACCUGCAC

CUAGUAUUCUCACUCCAG GUGCAUAGUUUCAUGCUCACAUA

AUUGGCAGGUGUGGC UU-3' simiR-153-1 ds-perfected
Oligo;
(SEQ ID NO: 7)
5'-AAGGCTCACAGCTGCCAGT TATGTGAGCATGAAACTATGCAC

CTAGTATTCTCACTCCAG GTGCATAGTTTCATGCTCACATA

ATTGGCAGGTGTGGCTATAGTGA-3'

Oligo is subjected to in vitro transcription (for
example but not limited to methods described
herein), CIP-treatment
Product;
(SEQ ID NO: 8)
5'-HO- GGGGGCUCACAGCUGCCAGU UAUGUGAGCAUGAAACUAUGCAC

CUAGUAUUCUCACUCCAG GUGCAUAGUUUCAUGCUCACAUA

AUUGGCAGGUGUGGC UU-3'

Example 5

Position 242-248 of APP 3' UTR hsa-miR-101

5'...AUUAAUGGGUUUUGUGUACUGUA...(SEQ ID NO: 9)
    |||||||
3'   AAGUCAAUAGUGUCAUGACAU  (SEQ ID NO: 10)

hsa-miR-101-1 original
(SEQ ID NO: 11)
UGCCCUGG CUCAGUUAUCACAGUGCUGAUGCU GUCUAUUCUAAAGG

UACAGUACUGUGAUAACUGAA GGAUGGCA simiR-101-1 perfect complement for APP
(SEQ ID NO: 12)
UGCCCUGG AUUAAUGGGUUUUGUGUACUGUA GUCUAUUCUAAAGG

UACAGUACACAAAACCCAUUAAU GGAUGGCA

DNA Oligo;
(SEQ ID NO: 13)
5'-AAGG TGCCCTGG ATTAATGGGTTTTGTGTACTGTA

GTCTATTCTAAAGG TACAGTACACAAAACCCATTAAT GGATGGCA

TATAGTGA-3'

↓ in vitro transcription, CIP-treatment
RNA Product;
(SEQ ID NO: 14)
5'-HO- GGGGG UGCCCUGG AUUAAUGGGUUUUGUGUACUGUA

GUCUAUUCUAAAGG UACAGUACACAAAACCCAUUAAU GGAUGGCA

UU-3'

Example 6

Position 457-463 of APP 3' UTR hsa-miR-153

5'...UUCCUUUCCUGAUCACUAUGCAU...(SEQ ID NO: 19)
    ||||    ||||||||
3' CUAGUGAAAACACU -GAUACGUU     (SEQ ID NO: 20)

hsa-miR-153-1 original
(SEQ ID NO: 15)
CUCACAGCUGCCAGU GUCAUUUUUGUGAUCUGCAG

CUAGUAUUCUCACUCCAG UUGCAUAGUCACAAAAGUGAUC

AUUGGCAGGUGUGGC

Hsa-miR-153-1 perfect complement for APP
(SEQ ID NO: 16)
CUCACAGCUGCCAGU UUCCUUUCCUGAUCACUAUGCAU

CUAGUAUUCUCACUCCAG AUGCAUAGUGAUCAGGAAAGGAA

AUUGGCAGGUGUGGC

DNA Oligo;
(SEQ ID NO: 17)
5'-AAGG CTCACAGCTGCCAGT TTCCTTTCCTGATCACTATGCAT

CTAGTATTCTCACTCCAG ATGCATAGTGATCAGGAAAGGAA

ATTGGCAGGTGTGGC TATAGTGA-3'

↓ in vitro transcription, CIP-treatment
RNA Product;
(SEQ ID NO: 18)
5'-HO- GGGGG CUCACAGCUGCCAGU

UUCCUUUCCUGAUCACUAUGCAU CUAGUAUUCUCACUCCAG

AUGCAUAGUGAUCAGGAAAGGAA AUUGGCAGGUGUGGC UU-3'

Example 7

Position 709-715 of APP 3' UTR hsa-miR-106a

5'...CCCUGUUCAUUGUAAGCACUUUU...(SEQ ID NO: 21)

|||||||||||

3' GAUGGACGUGACAUUCGUGAAAA (SEQ ID NO: 22)

hsa-miR- 106a original
(SEQ ID NO: 23)
CCUUGGCCAUGU AAAAGUGCUUACAGUGCAGGUAG CUUUUUGAGAU CUACUGCAAUGUAAGCACUUCUU ACAUUACCAUGG Hsa-miR-106a perfect complement for APP
(SEQ ID NO: 24)
CCUUGGCCAUGU AAAAGUGCUUACAAUGAACAGGG CUUUUUGAGAU CCCUGUUCAUUGUAAGCACUUUU ACAUUACCAUGG DNA Oligo;
(SEQ ID NO: 25)
5'-AAGG CCTTGGCCATGT AAAAGTGCTTACAATGAACAGGG CTTTTTGAGAT CCCTGTTCATTGTAAGCACTTTT ACATTACCATGG TATAGTGA-3'

↓ in vitro transcription, CIP-treatment
RNA Product;
(SEQ ID NO: 26)
5'-HO- GGGGG CCUUGGCCAUGU AAAAGUGCUUACAAUGAACAGGG CUUUUUGAGAU CCCUGUUCAUUGUAAGCACUUUU ACAUUACCAUGG UU-3'

Pre-smiR-XXX of the following sequence: 5'Gn-Nm-Ns-N*r-UU3' (SEQ ID NO: 27), wherein n=0-3, n=0-5, n=0-10, n=0, 1, 2, 3, 4, 5, 6, 7, 8, 9, 10; m, r=20-35; m, r=25-35; m, r=20-33; m, r=28-35; m, r=28-33; m, r=20, 21, 22, 23, 24, 25, 26, 27, 28, 29, 30, 31, 32, 33, 34, 35; s=20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, wherein the length of m, r, or s are determined by the number of nucleotides in the corresponding endogenous pre-miR-XXX; wherein the sequence of Ns is determined or the same as the loop in the endogenous pre-miRNA-XXX; wherein the sequence of Nm or N*r are as described herein. In certain embodiments the last two UU nucleotides are not present in the inventive pre-smiR-XXX sequences.

Example 8

Position 458-464 of SNCA 3' UTR

Position 458-464 of SNCA 3' UTR 5'...UAUGUGAGCAUGAAACUAUGCAC...(SEQ ID NO: 28)

||||||||||||||||| hsa-miR-153          3' CUAGUGAAAACACUGAUACGUU (SEQ ID NO: 29)

hsa-miR-153-1 natural Oligo;
(SEQ ID NO: 30)
5'-AAGGCTCACAGCTGCCAGT GTCATTTTTGTGATCTGCAG CTAGTATTCTCACTCCAG TTGCATAGTCACAAAAGTGATC ATTGGCAGGTGTGGCTATAGTGA-3'

<<in vitro transcription, CIP-treatment
Product;
(SEQ ID NO: 31)
5'-HO- GGGGGCUCACAGCUGCCAGU GUCAUUUUUGUGAUCUGCAG CUAGUAUUCUCACUCCAG UUGCAUAGUCACAAAAGUGAUC AUUGGCAGGUGUGGC UU-3' simiR153-1 ss-perfected Oligo;
(SEQ ID NO: 32)
5'-AAGGCTCACAGCTGCCAGT TTGTGAGCATGAAACCTGCAC CTAGTATTCTCACTCCAG GTGCATAGTTTCATGCTCACATA ATTGGCAGGTGTGGCTATAGTGA-3'

<<in vitro transcription, CIP-treatment
Product;
(SEQ ID NO: 33)
5'-HO- GGGGGCUCACAGCUGCCAGU UUGUGAGCAUGAAACCUGCAC CUAGUAUUCUCACUCCAG GUGCAUAGUUUCAUGCUCACAUA AUUGGCAGGUGUGGC UU-3' simiR-153-1 ds-perfected Oligo;
(SEQ ID NO: 105)
5'-AAGGCTCACAGCTGCCAGT TATGTGAGCATGAAACTATGCAC CTAGTATTCTCACTCCAG GTGCATAGTTTCATGCTCACATA ATTGGCAGGTGTGGCTATAGTGA-3'

<<in vitro transcription, CIP-treatment
Product;
(SEQ ID NO: 34)
5'-HO- GGGGGCUCACAGCUGCCAGU UAUGUGAGCAUGAAACUAUGCA CCUAGUAUUCUCACUCCAG GUGCAUAGUUUCAUGCUCACAUA AUUGGCAGGUGUGGC UU-3'

Example 9

```
Position 119-125 of SNCA 3' UTR

Position 119-125 of SNCA 3' UTR  5'...ACAGUGUAUCUCGAAGUCUUCCA...(SEQ ID NO: 35)
                                        |||  ||||||
hsa-miR-7                            3' UGUUGUUUUAGUGAU-CAGAAGGU(SEQ ID NO: 36)
``` hsa-miR-7-2 natural
Oligo;
(SEQ ID NO: 37)
5'-AAGGCTGGATACAGAGTGGACCGGCTGGCCCCATC

TGGAAGACTAGTGATTTTGTTGT TGTCTTACTGCGCTCA

-continued

ACAACAAATCCCAGTCTACCT AATGGTGCCAGCCATCGCA

TATAGTGA-3'

<<in vitro transcription, CIP-treatment
Product;
(SEQ ID NO: 38)
5'-HO-GGGGGCUGGAUACAGAGUGGACCGGCUGGCCCCAUC

UGGAAGACUAGUGAUUUUGUUGU UGUCUUACUGCGCUCA

ACAACAAAUCCCAGUCUACCU AAUGGUGCCAGCCAUCGCA UU-3' si2miR7-2 ss-perfected
Oligo;
(SEQ ID NO: 39)
5'-AAGGCTGGATACAGAGTGGACCGGCTGGCCCCATC

TGGAAGACTTCGAGATACACTGT TGTCTTACTGCGCTCA

ACAGTTATCTATAGTCTACCT AATGGTGCCAGCCATCGCA

TATAGTGA-3'

<<in vitro transcription, CIP-treatment
Product;
(SEQ ID NO: 40)
5'-HO-GGGGGCUGGAUACAGAGUGGACCGGCUGGCCCCAUC

UGGAAGACUUCGAGAUACACUGU UGUCUUACUGCGCUCA

ACAGUUAUCUAUAGUCUACCU AAUGGUGCCAGCCAUCGCA UU-3' simiR7-2 ds-perfected
Oligo;
(SEQ ID NO: 41)
5'-AAGGCTGGATACAGAGTGGACCGGCTGGCCCCATC

TGGAAGACTTCGAGATACACTGT TGTCTTACTGCGCTCA

ACAGTGTATCTCGAAGTCTTCCA AATGGTGCCAGCCATCGCA

TATAGTGA-3'

<<in vitro transcription, CIP-treatment
Product;
(SEQ ID NO: 42)
5'-HO-GGGGGCUGGAUACAGAGUGGACCGGCUGGCCCCAUC -continued

UGGAAGACUUCGAGAUACACUGU UGUCUUACUGCGCUCA

ACAGUGUAUCUCGAAGUCUUCCA AAUGGUGCCAGCCAUCGCA UU-3'

Example 10

```
Position 416-422 of SNCA 3' UTR

Position 416-422 of SNCA 3' UTR  5'...UGACGUAUUGUGAAAUUUGUUAA...(SEQ ID NO: 43)
                                        |||||||||||||||
hsa-miR-495                          3' UUCUUCACGUGGUACAAACAAA (SEQ ID NO: 44)
``` hsa-miR-495 natural
Oligo;
(SEQ ID NO: 45)
5'-AAGGTGGTACCTGAA AAGAAGTTGCCCAUGTTATTTT

CGCTTTATATGTGACG AAACAAACATGGTGCACTTCTT

TTTCGGTATCATATAGTGA-3'

<<in vitro transcription, CIP-treatment
Product;
(SEQ ID NO: 46)
5'-HO-GGGGGUGGUACCUGAA AAGAAGUUGCCCAUGUUAUUUU

CGCUUUAUAUGUGACG AAACAAACAUGGUGCACUUCUU

UUUCGGUAUCA UU-3' simiR495 ss-perfected
Oligo;
(SEQ ID NO: 47)
5'-AAGGTGGTACCTGAA TGACGTAGTTTGAAATTACTTA

CGCTTTATATGTGACG TAACAAATTTCACAATACGTCA

TTTCGGTATCATATAGTGA-3'

<<in vitro transcription, CIP-treatment
Product;
(SEQ ID NO: 48)
5'-HO-GGGGGUGGUACCUGAA UGACGUAGUUUGAAAUUACUUA

CGCUUUAUAUGUGACG UAACAAAUUUCACAAUACGUCA

UUUCGGUAUCA UU-3' simiR-495 ds-perfected
Oligo;
(SEQ ID NO: 49)
5'-AAGGTGGTACCTGAA TGACGTATTGTGAAATTTGTTAA

CGCTTTATATGTGACG TTAACAAATTTCACAATACGTCA

TTTCGGTATCATATAGTGA-3'

<<in vitro transcription, CIP-treatment
Product;
(SEQ ID NO: 50)
5'-HO-GGGGGUGGUACCUGAA UGACGUAUUGUGAAAUUUGUUAA

CGCUUUAUAUGUGACG UUAACAAAUUUCACAAUACGUCA

UUUCGGUAUCA UU-3'

Example 11

Position 458-464 of SNCA 3' UTR
Position 458-464 of SNCA 3' UTR 5' ... UAUGUGAGCAUGAAACUAUGCAC ...(SEQ ID NO:51)
                                          ||||||||
            hsa-miR-153        3'     CUAGUGAAAACACUGAUACGUU    (SEQ ID NO:52)

hsa-miR-153-1 natural
(SEQ ID NO: 53)
Oligo; 5'-AAGGCTCACAGCTGCCAGT GTCATTTTTGTGATCTGCAG

CTAGTATTCTCACTCCAG TTGCATAGTCACAAAAGTGATC

ATTGGCAGGTGTGGC TATAGTGA-3'

↓ in vitro transcription, CIP-treatment (SEQ ID NO: 54)
Product; 5'-HO-GGGGGCUCACAGCUGCCAGU

GUCAUUUUUGUGAUCUGCAG CUAGUAUUCUCACUCCAG

UUGCAUAGUCACAAAAGUGAUC AUUGGCAGGUGUGGC UU-3' simiR153-1 ss-perfected
(SEQ ID NO: 55)
Oligo; 5'-AAGGCTCACAGCTGCCAGT

TTGTGAGCATGAAACCTGCAC CTAGTATTCTCACTCCAG

GTGCATAGTTTCATGCTCACATA ATTGGCAGGTGTGGC

TATAGTGA-3'

↓ in vitro transcription, CIP-treatment (SEQ ID NO: 56)
Product; 5'-HO-GGGGGCUCACAGCUGCCAGU

UUGUGAGCAUGAAACCUGCAC CUAGUAUUCUCACUCCAG

GUGCAUAGUUUCAUGCUCACAUA AUUGGCAGGUGUGGC UU-3' simiR-153-1 ds-perfected
(SEQ ID NO: 57)
Oligo; 5'-AAGGCTCACAGCTGCCAGT

TATGTGAGCATGAAACTATGCAC CTAGTATTCTCACTCCAG

GTGCATAGTTTCATGCTCACATA ATTGGCAGGTGTGGC

TATAGTGA-3'

↓ in vitro transcription, CIP-treatment (SEQ ID NO: 58)
Product; 5'-HO-GGGGGCUCACAGCUGCCAGU

UAUGUGAGCAUGAAACUAUGCAC CUAGUAUUCUCACUCCAG

GUGCAUAGUUUCAUGCUCACAUA AUUGGCAGGUGUGGC UU-3'

Example 12

Position 119-125 of SNCA 3' UTR
Position 119-125 of SNCA 3' UTR 5' ... ACAGUGUAUCUCGAAGUCUUCCA ...(SEQ ID NO:59)
                                         |||    |||||||
            hsa-miR-7            3'     UGUUGUUUUAGUGAU-CAGAAGGU  (SEQ ID NO:60)

hsa-miR-7-2 natural
(SEQ ID NO: 61)
Oligo; 5'-AAGGCTGGATACAGAGTGGACCGGCTGGCCCCATC

TGGAAGACTAGTGATTTTGTTGT TGTCTTACTGCGCTCA

ACAACAAATCCCAGTCTACCT AATGGTGCCAGCCATCGCA

TATAGTGA-3'

↓ in vitro transcription, CIP-treatment (SEQ ID NO: 62)
Product;

5'-HO-GGGGGCUGGAUACAGAGUGGACCGGCUGGCCCCAUC

UGGAAGACUAGUGAUUUUGUUGU UGUCUUACUGCGCUCA

ACAACAAUCCCAGUCUACCU AAUGGUGCCAGCCAUCGCA UU-3' si2miR7-2 ss-perfected
(SEQ ID NO: 63)
Oligo; 5'-AAGGCTGGATACAGAGTGGACCGGCTGGCCCCATC

TGGAAGACTTCGAGATACACTGT TGTCTTACTGCGCTCA

ACAGTTATCTATAGTCTACCT AATGGTGCCAGCCATCGCA

TATAGTGA-3'

↓ in vitro transcription, CIP-treatment (SEQ ID NO: 64)
Product;

5'-HO-GGGGGCUGGAUACAGAGUGGACCGGCUGGCCCCAUC

-continued

UGGAAGACUUCGAGAUACACUGU UGUCUUACUGCGCUCA

ACAGUUAUCUAUAGUCUACCU AAUGGUGCCAGCCAUCGCA UU-3' simiR7-2 ds-perfected (SEQ ID NO: 65)
Oligo; 5'-AAGGCTGGATACAGAGTGGACCGGCTGGCCCCATC

TGGAAGACTTCGAGATACACTGT TGTCTTACTGCGCTCA

ACAGTGTATCTCGAAGTCTTCCA AATGGTGCCAGCCATCGCA

TATAGTGA-3'

↓in vitro transcription, CIP-treatment (SEQ ID NO: 66)
Product;
5'-HO-GGGGGCUGGAUACAGAGUGGACCGGCUGGCCCCAUC

UGGAAGACUUCGAGAUACACUGU UGUCUUACUGCGCUCA

ACAGUGUAUCUCGAAGUCUUCCA AAUGGUGCCAGCCAUCGCA UU-3'

Example 13

Position 416-422 of SNCA 3' UTR
Position 416-422 of SNCA 3' UTR 5' ...UGACGUAUUGUGAAAUUUGUUAA... (SEQ ID NO: 67)
                                          |||||
                    hsa-miR-495 3'     UUCUUCACGUGGUACAAACAAA     (SEQ ID NO: 68)

hsa-miR-495 natural
(SEQ ID NO: 69)
Oligo; 5'-AAGGTGGTACCTGAA AAGAAGTTGCCCAUGTTATTTT

CGCTTTATATGTGACG AAACAAACATGGTGCACTTCTT

TTTCGGTATCA TATAGTGA-3'

↓in vitro transcription, CIP-treatment (SEQ ID NO: 70)
Product; 5'-HO-GGGGGUGGUACCUGAA

AAGAAGUUGCCCAUGUUAUUUU CGCUUUAUAUGUGACG

AAACAAACAUGGUGCACUUCUU UUUCGGUAUCA UU-3' simiR495 ss-perfected (SEQ ID NO: 71)
Oligo; 5'-AAGGTGGTACCTGAA TGACGTAGTTTGAAATTACTTA

CGCTTTATATGTGACG TAACAAATTTCACAATACGTCA

TTTCGGTATCA TATAGTGA-3'

↓in vitro transcription, CIP-treatment (SEQ ID NO: 106)
Product; 5'-HO-GGGGGUGGUACCUGAA

UGACGUAGUUUGAAAUUACUUA CGCUUUAUAUGUGACG

UAACAAAUUUCACAAUACGUCA UUUCGGUAUCA UU-3' simiR-495 ds-perfected (SEQ ID NO: 107)
Oligo; 5'-AAGGTGGTACCTGAA TGACGTATTGTGAAATTTGTTAA

CGCTTTATATGTGACG TTAACAAATTTCACAATACGTCA

TTTCGGTATCA TATAGTGA-3'

↓in vitro transcription, CIP-treatment

-continued (SEQ ID NO: 72)
Product; 5'-HO-GGGGGUGGUACCUGAA

UGACGUAUUGUGAAAUUUGUUAA CGCUUUAUAUGUGACG

UUAACAAAUUUCACAAUACGUCA UUUCGGUAUCA UU-3'

Example 14

Position 242-248 of APP 3' UTR
hsa-miR-101 5' ...AUUAAUGGGUUUUGUGUACUGUA... (SEQ ID NO: 73)
                                 |||||
            3'     AAGUCAAUAGUGUCAUGACAU     (SEQ ID NO: 74)

hsa-miR-101-1 original (SEQ ID NO: 75)
UGCCCUGG CUCAGUUAUCACAGUGCUGAUGCU GUCUAUUCUAAAGG

UACAGUACUGUGAUAACUGAA GGAUGGCA simiR-101-1 perfect complement for APP (SEQ ID NO: 76)

UGCCCUGG AUUAAUGGGUUUUGUGUACUGUA GUCUAUUCUAAAGG

UACAGUACACAAAACCCAUUAAU GGAUGGCA (SEQ ID NO: 77)

DNA Oligo; 5'-AAGG TGCCCTGG

ATTAATGGGTTTTGTGTACTGTA GTCTATTCTAAAGG

TACAGTACACAAAACCCATTAAT GGATGGCA TATAGTGA-3'

↓ in vitro transcription, CIP-treatment (SEQ ID NO: 78)

RNA Product; 5'-HO-GGGGG UGCCCUGG

AUUAAUGGGUUUUGUGUACUGUA GUCUAUUCUAAAGG

UACAGUACACAAAACCCAUUAAU GGAUGGCA UU-3'

Example 15

Position 457-463 of APP 3' UTR hsa-miR-153 5'... UUCCUUUCCUGAUCACUAUGCAU...(SEQ ID NO:79)

3'    CUAGUGAAACACU---GAUACGUU   (SEQ ID NO:80)

hsa-miR-153-1 original (SEQ ID NO: 81)

CUCACAGCUGCCAGU GUCAUUUUGUGAUCUGCAG

CUAGUAUUCUCACUCCAG UUGCAUAGUCACAAAAGUGAUC

AUUGGCAGGUGUGGC

Hsa-miR-153-1 perfect complement for APP (SEQ ID NO: 82)

CUCACAGCUGCCAGU UUCCUUUCCUGAUCACUAUGCAU

CUAGUAUUCUCACUCCAG AUGCAUAGUGAUCAGGAAAGGAA

AUUGGCAGGUGUGGC (SEQ ID NO: 83)

DNA Oligo; 5'-AAGG CTCACAGCTGCCAGT

TTCCTTTCCTGATCACTATGCAT CTAGTATTCTCACTCCAG

ATGCATAGTGATCAGGAAAGGAA ATTGGCAGGTGTGGC

TATAGTGA-3'

↓ in vitro transcription, CIP-treatment (SEQ ID NO: 84)

RNA Product; 5'-HO-GGGGG CUCACAGCUGCCAGU

UUCCUUUCCUGAUCACUAUGCAU CUAGUAUUCUCACUCCAG

AUGCAUAGUGAUCAGGAAAGGAA AUUGGCAGGUGUGGC UU-3'

Example 16

Position 709-715 of APP 3' UTR hsa-miR-106A 5'... CCCUGUUCAUUGUAAGCACUUUU...(SEQ ID NO:85)

3'    GAUGGACGUGACAUUCGUGAAAA   (SEQ ID NO:86)

hsa-miR-106a original (SEQ ID NO: 87)

CCUUGGCCAUGU AAAAGUGCUUACAGUGCAGGUAG CUUUUUGAGAU

CUACUGCAAUGUAAGCACUUCUU ACAUUACCAUGG

Hsa-miR-106a perfect complement for APP (SEQ ID NO: 88)

CCUUGGCCAUGU AAAAGUGCUUACAAUGAACAGGG CUUUUUGAGAU

CCCUGUUCAUUGUAAGCACUUUU ACAUUACCAUGG (SEQ ID NO: 89)

DNA Oligo; 5'-AAGG CCTTGGCCATGT

AAAAGTGCTTACAATGAACAGGG CTTTTTGAGAT

CCCTGTTCATTGTAAGCACTTTT ACATTACCATGG TATAGTGA-3'

↓ in vitro transcription, CIP-treatment (SEQ ID NO: 90)

RNA Product; 5'-HO-GGGGG CCUUGGCCAUGU

AAAAGUGCUUACAAUGAACAGGG CUUUUUGAGAU

CCCUGUUCAUUGUAAGCACUUUU ACAUUACCAUGG UU-3'

TABLE 1

|  | Control Patients | | | PD Patients | | |
| --- | --- | --- | --- | --- | --- | --- |
|  | Cortex | Midbrain | Cerebellum | Cortex | Midbrain | Cerebellum |
| pre-miR101-1 | 0.12 | 1.00 | 1.13 | 0.02 | 0.02 | 0.47 |
| pre-miR106b | 1.01 | 1.00 | 1.25 | 1.27 | 0.27 | 1.37 |
| pre-miR16-1 | 0.10 | 1.00 | 1.58 | 0.28 | 0.22 | 0.82 |
| pre-miR338 | 0.46 | 1.00 | 0.42 | 0.85 | 0.38 | 0.49 |
| pre-miR93 | 0.22 | 1.00 | 1.15 | 0.37 | 0.34 | 0.87 |
| pre-miR148a | 0.60 | 1.00 | 0.91 | 0.29 | 0.43 | 0.28 |
| pre-miR324 | 0.66 | 1.00 | 1.30 | 0.89 | 0.36 | 2.61 |
| pre-miR374 | 0.51 | 1.00 | 1.17 | 0.34 | 0.49 | 2.41 |

What is claimed is:

1. An engineered mammalian pre-microRNA comprising SEQ ID NO: 6, 8, 12, 14, 16, 18, 24, 26, 33, 34, 40, 42, 48, or 50.

2. A therapeutic composition for intracerebral delivery comprising a pre-microRNA comprising SEQ ID NOs: 6, 8, 12, 14, 16, 18, 24, 26, 33, 34, 40, 42, 48, or 50, or any combination thereof.

3. A method to reduce aSyn levels in a cell or in a subject in need thereof comprising administering to a cell or a subject in need thereof a therapeutic amount of a pre-micro RNA smiR-7-2(SNCA) comprising SEQ ID NO: 40 or 42, a pre-micro RNA smiR-153-1(SNCA) comprising SEQ ID NO: 6 or 8, a pre-micro RNA smiR-495(SNCA) comprising SEQ ID NO: 48 or 50, or any combination thereof.

4. A method to treat Parkinson's Disease in a subject in need thereof comprising administering to a subject in need thereof a therapeutic amount of a pre-micro RNA smiR-7-2(SNCA) comprising SEQ ID NO: 40 or 42, a pre-micro RNA smiR-153-1(SNCA) comprising SEQ ID NO: 6 or 8, a pre-micro RNA smiR-495(SNCA) comprising SEQ ID NO: 48 or 50, or any combination thereof.

5. A method to rescue or increase survival of dopaminergic neurons in a subject in need thereof comprising administering to a subject in need thereof a therapeutic amount of a pre-micro RNA smiR-7-2(SNCA) comprising SEQ ID NO: 40 or 42, a pre-micro RNA smiR-153-1(SNCA) comprising SEQ ID NO: 6 or 8, a pre-micro RNA smiR-495(SNCA) comprising SEQ ID NO: 48 or 50, or any combination thereof.

6. A method to rescue or increase survival of a dopaminergic neuron comprising contacting the neuron with a therapeutic amount of a pre-micro RNA smiR-7-2(SNCA) comprising SEQ ID NO: 40 or 42, a pre-micro RNA smiR-153-1(SNCA) comprising SEQ ID NO: 6 or 8, a pre-micro RNA smiR-495(SNCA) comprising SEQ ID NO: 48 or 50, or any combination thereof.

7. A method to reduce APP levels in a cell or in a subject in need thereof comprising administering to a cell or a subject in need thereof a therapeutic amount of a pre-micro RNA smiR-106(a)(APP) comprising SEQ ID NO: 26, a pre-micro RNA smiR-153(APP) comprising SEQ ID NO: 18, a smiR-101-1 (APP) comprising SEQ ID NO: 14, or any combination thereof.

8. A method to treat Alzheimer's disease in a subject in need thereof comprising administering to a subject in need thereof a therapeutic amount of a pre-micro RNA smiR-106 (a)(APP) comprising SEQ ID NO: 26, a pre-micro RNA smiR-153(APP) comprising SEQ ID NO: 18, a smiR-101-1 (APP) comprising SEQ ID NO: 14, or any combination thereof.

* * * * *

SEQUENCE LISTING

<160> NUMBER OF SEQ ID NOS: 108

<210> SEQ ID NO 1
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
uaugugagca ugaaacuaug cac                                              23

<210> SEQ ID NO 2
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
uugcauaguc acaaaaguga uc                                               22

<210> SEQ ID NO 3
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
aaggctcaca gctgccagtg tcatttttgt gatctgcagc tagtattctc actccagttg      60
catagtcaca aaagtgatca ttggcaggtg tggctatagt ga                        102

<210> SEQ ID NO 4
<211> LENGTH: 97
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
gggggcucac agcugccagu gucauuuuug ugaucugcag cuaguauucu cacuccaguu      60
gcauagucac aaaagugauc auuggcaggu guggcuu                              97

<210> SEQ ID NO 5
<211> LENGTH: 104

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
aaggctcaca gctgccagtt tgtgagcatg aaacctgcac ctagtattct cactccaggt      60
gcatagtttc atgctcacat aattggcagg tgtggctata gtga                      104

<210> SEQ ID NO 6
<211> LENGTH: 99
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
gggggcucac agcugccagu uugugagcau gaaaccugca ccuaguauuc ucacuccagg      60
ugcauaguuu caugcucaca uaauuggcag guguggcuu                            99

<210> SEQ ID NO 7
<211> LENGTH: 106
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
aaggctcaca gctgccagtt atgtgagcat gaaactatgc acctagtatt ctcactccag      60
gtgcatagtt tcatgctcac ataattggca ggtgtggcta tagtga                    106

<210> SEQ ID NO 8
<211> LENGTH: 101
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 8
gggggcucac agcugccagu uaugugagca ugaaacuaug caccuaguau ucucacucca      60
ggtgcauagu uucaugcuca cauaauuggc aggtguggcu u                         101

<210> SEQ ID NO 9
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
auuaaugggu uuguguacu gua                                              23

<210> SEQ ID NO 10
<211> LENGTH: 21
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 10
uacaguacug ugauaacuga a                                           21

<210> SEQ ID NO 11
<211> LENGTH: 75
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
ugcccuggcu caguuaucac agugcugaug cugucuauuc uaaagguaca guacugugau    60
aacugaagga uggca                                                    75

<210> SEQ ID NO 12
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 12
ugcccuggat taatgggttt tgtgtactgt agucuauucu aaaggtacag tacacaaaac    60
ccattaatgg auggca                                                   76

<210> SEQ ID NO 13
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
aaggtgccct ggattaatgg gttttgtgta ctgtagtcta ttctaaaggt acagtacaca    60
aaacccatta atggatggca tatagtga                                      88

<210> SEQ ID NO 14
<211> LENGTH: 83
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
gggggugccc uggauuaaug gguuuugugu acuguagucu auucuaaagg uacaguacac    60 aaacccauu aauggauggc auu                                            83

<210> SEQ ID NO 15
<211> LENGTH: 90
<212> TYPE: RNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 15
cucacagcug ccagugucau uuuugugauc ugcagcuagu auucucacuc caguugcaua    60
gucacaaaag ugaucauugg caggugudgc                                    90

<210> SEQ ID NO 16
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 16
cucacagcug ccaguuucct ttcctgatca ctatgcatcu aguauucuca cuccagatgc    60
atagtgatca ggaaggaaa uuggcaggug uggc                                94

<210> SEQ ID NO 17
<211> LENGTH: 106
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
aaggctcaca gctgccagtt tcctttcctg atcactatgc atctagtatt ctcactccag    60
atgcatagtg atcaggaaag gaaattggca ggtgtggcta tagtga                 106

<210> SEQ ID NO 18
<211> LENGTH: 101
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 18
gggggcucac agcugccagu uccuuuccu gaucacuaug caucuaguau ucucacucca    60
gaugcauagu gaucaggaaa ggaaauuggc aggguguggcu u                     101

<210> SEQ ID NO 19
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
uuccuuuccu gaucacuaug cau                                           23

<210> SEQ ID NO 20
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
uugcauaguc acaaaaguga uc                                            22
```

-continued

<210> SEQ ID NO 21
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
cccuguucau uguaagcacu uuu                                            23

<210> SEQ ID NO 22
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
aaaagugcuu acagugcagg uag                                            23

<210> SEQ ID NO 23
<211> LENGTH: 81
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
ccuuggccau guaaaagugc uuacagugca gguagcuuuu ugagaucuac ugcaauguaa    60
gcacuucuua cauuaccaug g                                              81

<210> SEQ ID NO 24
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 24
ccuuggccau guaaaagtgc ttacaatgaa cagggcuuuu ugagauccct gttcattgta    60
agcactttta cauuaccaug g                                              81

<210> SEQ ID NO 25
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
aaggccttgg ccatgtaaaa gtgcttacaa tgaacagggc tttttgagat ccctgttcat    60
tgtaagcact tttacattac catggtatag tga                                 93

<210> SEQ ID NO 26
<211> LENGTH: 88
<212> TYPE: RNA

<213> ORGANISM: Artificial Sequence
<220> FEATURE:
<223> OTHER INFORMATION: Description of Artificial Sequence: Synthetic
      oligonucleotide

<400> SEQUENCE: 26
gggggccuug gccauguaaa agugcuuaca augaacaggg cuuuugaga ucccuguuca        60 uuguaagcac uuuuacauua ccaugguu                                          88

<210> SEQ ID NO 27
<211> LENGTH: 147
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: misc_feature
<222> LOCATION: (1)..(10)
<223> OTHER INFORMATION: This region may encompass 0-3, 0-5, 0-10, or 0,
      1, 2, 3, 4, 5, 6, 7, 8, 9, or 10 nucleotides
<220> FEATURE:
<221> NAME/KEY: modified_base
<222> LOCATION: (11)..(45)
<223> OTHER INFORMATION: a, c, t, g, unknown or other and this region
      may encompass 20-35, 25-35, 20-33, 28-35, 28-33, or 20, 21, 22,
      23, 24, 25, 26, 27, 28, 29, 30, 31, 32, 33, 34, or 35 nucleotides
<220> FEATURE:
<221> NAME/KEY: modified_base
<222> LOCATION: (46)..(110)
<223> OTHER INFORMATION: a, c, t, g, unknown or other; this region may
      encompass 20, 21, 22, 23, 24, 25, 26, 27, 28, 29, 30, 31, 32, 33,
      34, 35, 36, 37, 38, 39, 40, 41, 42, 43, 44, 45, 46, 47, 48, 49,
      50, 51, 52, 53, 54, 55, 56, 57, 58, 59, 60, 61, 62, 63, 64, or 65
      nucleotides
<220> FEATURE:
<221> NAME/KEY: modified_base
<222> LOCATION: (111)..(145)
<223> OTHER INFORMATION: a, c, t, g, unknown or other and this region
      may encompass 20-35, 25-35, 20-33, 28-35, 28-33, or 20, 21, 22,
      23, 24, 25, 26, 27, 28, 29, 30, 31, 32, 33, 34, or 35 nucleotides
<220> FEATURE:
<223> OTHER INFORMATION: see specification as filed for detailed
      description of substitutions and preferred embodiments

<400> SEQUENCE: 27
gggggggggg nnnnnnnnnn nnnnnnnnnn nnnnnnnnnn nnnnnnnnnn nnnnnnnnnn        60
nnnnnnnnnn nnnnnnnnnn nnnnnnnnnn nnnnnnnnnn nnnnnnnnnn nnnnnnnnnn       120
nnnnnnnnnn nnnnnnnnnn nnnnnuu                                           147

<210> SEQ ID NO 28
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
uaugugagca ugaaacuaug cac                                               23

<210> SEQ ID NO 29
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 29
uugcauaguc acaaaaguga uc                                              22

<210> SEQ ID NO 30
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
aaggctcaca gctgccagtg tcattttttgt gatctgcagc tagtattctc actccagttg    60
catagtcaca aaagtgatca ttggcaggtg tggctatagt ga                       102

<210> SEQ ID NO 31
<211> LENGTH: 97
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
gggggcucac agcugccagu gucauuuuug ugaucugcag cuaguauucu cacuccaguu    60
gcauagucac aaaagugauc auuggcaggu guggcuu                             97

<210> SEQ ID NO 32
<211> LENGTH: 104
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
aaggctcaca gctgccagtt tgtgagcatg aaacctgcac ctagtattct cactccaggt    60
gcatagtttc atgctcacat aattggcagg tgtggctata gtga                    104

<210> SEQ ID NO 33
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 33
gggggcucac agcugccagu uugugagcau gaaaccugca ccuaguauuc ucacuccagg    60
ugcauaguuu catgcucaca uaauuggcag guguggcuu                           99

<210> SEQ ID NO 34
<211> LENGTH: 101
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 34
gggggcucac agcugccagu uaugugagca ugaaacuaug caccuaguau ucucacucca    60
ggugcauagu uucaugcuca cauaauuggc aggguguggcu u                       101

<210> SEQ ID NO 35
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
acaguguauc ucgaagucuu cca                                            23

<210> SEQ ID NO 36
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
uggaagacua gugauuuugu ugu                                            23

<210> SEQ ID NO 37
<211> LENGTH: 122
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
aaggctggat acagagtgga ccggctggcc ccatctggaa gactagtgat tttgttgttg    60
tcttactgcg ctcaacaaca aatcccagtc tacctaatgg tgccagccat cgcatatagt    120
ga                                                                   122

<210> SEQ ID NO 38
<211> LENGTH: 117
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 38
gggggcugga uacagagugg accggcuggc cccaucugga agacuaguga uuuuguuguu    60
gucuuacugc gcucaacaac aaaucccagu cuaccuaaug gugccagcca ucgcauu       117

<210> SEQ ID NO 39
<211> LENGTH: 122
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
aaggctggat acagagtgga ccggctggcc ccatctggaa gacttcgaga tacactgttg    60

```
tcttactgcg ctcaacagtt atctatagtc tacctaatgg tgccagccat cgcatatagt    120
ga                                                                  122
```

<210> SEQ ID NO 40
<211> LENGTH: 117
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 40

```
gggggcugga uacagagugg accggcuggc cccaucugga agacuucgag auacacuguu    60
gucuuacugc gcucaacagu uaucuauagu cuaccuaaug gugccagcca ucgcauu       117
```

<210> SEQ ID NO 41
<211> LENGTH: 124
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41

```
aaggctggat acagagtgga ccggctggcc ccatctggaa gacttcgaga tacactgttg    60
tcttactgcg ctcaacagtg tatctcgaag tcttccaaat ggtgccagcc atcgcatata   120
gtga                                                                124
```

<210> SEQ ID NO 42
<211> LENGTH: 119
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 42

```
gggggcugga uacagagugg accggcuggc cccaucugga agacuucgag auacacuguu    60
gucuuacugc gcucaacagu guaucucgaa gucuuccaaa uggugccagc caucgcauu    119
```

<210> SEQ ID NO 43
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43

```
ugacguauug ugaaauuugu uaa                                            23
```

<210> SEQ ID NO 44
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 44
aaacaaacau ggugcacuuc uu                                              22

<210> SEQ ID NO 45
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 45
aaggtggtac ctgaaaagaa gttgcccaug ttattttcgc tttatatgtg acgaaacaaa     60
catggtgcac ttcttttttcg gtatcatata gtga                                94

<210> SEQ ID NO 46
<211> LENGTH: 89
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46 gggggguggua ccugaaaaga aguugcccau guuauuuucg cuuuauaugu gacgaaacaa    60
acauggugca cuucuuuuuc gguaucauu                                       89

<210> SEQ ID NO 47
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
aaggtggtac ctgaatgacg tagtttgaaa ttacttacgc tttatatgtg acgtaacaaa     60
tttcacaata cgtcatttcg gtatcatata gtga                                 94

<210> SEQ ID NO 48
<211> LENGTH: 89
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48 gggggguggua ccugaaugac guaguuugaa auuacuuacg cuuuauaugu gacguaacaa    60
auuucacaau acgucauuuc gguaucauu                                       89

<210> SEQ ID NO 49
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
aaggtggtac ctgaatgacg tattgtgaaa tttgttaacg ctttatatgt gacgttaaca    60
```
aatttcacaa tacgtcattt cggtatcata tagtga     96

<210> SEQ ID NO 50
<211> LENGTH: 91
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
ggggguggua ccugaaugac guauugugaa auuuguuaac gcuuuauaug ugacguuaac     60
aaauuucaca auacgucauu ucgguaucau u     91

<210> SEQ ID NO 51
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
uaugugagca ugaaacuaug cac     23

<210> SEQ ID NO 52
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
uugcauaguc acaaaaguga uc     22

<210> SEQ ID NO 53
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
aaggctcaca gctgccagtg tcatttttgt gatctgcagc tagtattctc actccagttg     60
catagtcaca aaagtgatca ttggcaggtg tggctatagt ga     102

<210> SEQ ID NO 54
<211> LENGTH: 97
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54 ggggcucac agcugccagu gucauuuuug ugaucugcag cuaguauucu cacuccaguu     60 gcauaguca c aaaagugauc auuggcaggu guggcuu     97

<210> SEQ ID NO 55
<211> LENGTH: 104
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 55
aaggctcaca gctgccagtt tgtgagcatg aaacctgcac ctagtattct cactccaggt   60
gcatagtttc atgctcacat aattggcagg tgtggctata gtga   104

<210> SEQ ID NO 56
<211> LENGTH: 99
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 56
gggggcucac agcugccagu uugugagcau gaaaccugca ccuaguauuc ucacuccagg   60
ugcauaguuu catgcucaca uaauuggcag guggcuu   99

<210> SEQ ID NO 57
<211> LENGTH: 106
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 57
aaggctcaca gctgccagtt atgtgagcat gaaactatgc acctagtatt ctcactccag   60
gtgcatagtt tcatgctcac ataattggca ggtgtggcta tagtga   106

<210> SEQ ID NO 58
<211> LENGTH: 101
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 58
gggggcucac agcugccagu uatgugagca ugaaacuaug caccuaguau ucucacucca   60
ggugcauagu uucaugcuca cauaauuggc aggugugcu u   101

<210> SEQ ID NO 59
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 59
acaguguauc ucgaagucuu cca   23

<210> SEQ ID NO 60
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
uggaagacua gugauuuugu ugu                                           23

<210> SEQ ID NO 61
<211> LENGTH: 122
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
aaggctggat acagagtgga ccggctggcc ccatctggaa gactagtgat tttgttgttg   60
tcttactgcg ctcaacaaca aatcccagtc tacctaatgg tgccagccat cgcatatagt  120
ga                                                                 122

<210> SEQ ID NO 62
<211> LENGTH: 117
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 62
gggggcugga uacagagugg accggcuggc cccaucugga agacuaguga uuuguugu    60 gucuuacugc gcucaacaac aaaucccagu cuaccuaaug gugccagcca ucgcauu     117

<210> SEQ ID NO 63
<211> LENGTH: 122
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63
aaggctggat acagagtgga ccggctggcc ccatctggaa gacttcgaga tacactgttg   60
tcttactgcg ctcaacagtt atctatagtc tacctaatgg tgccagccat cgcatatagt  120
ga                                                                 122

<210> SEQ ID NO 64
<211> LENGTH: 117
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 64
gggggcugga uacagagugg accggcuggc cccaucugga agacuucgag auacacuguu   60
gucuuacugc gcucaacagu uaucuauagu cuaccuaaug gugccagcca ucgcauu     117

<210> SEQ ID NO 65
<211> LENGTH: 124
<212> TYPE: DNA

<213> ORGANISM: Artificial Sequence
<220> FEATURE:
<223> OTHER INFORMATION: Description of Artificial Sequence: Synthetic
      polynucleotide

<400> SEQUENCE: 65
aaggctggat acagagtgga ccggctggcc ccatctggaa gacttcgaga tacactgttg     60
tcttactgcg ctcaacagtg tatctcgaag tcttccaaat ggtgccagcc atcgcatata    120
gtga                                                                 124

<210> SEQ ID NO 66
<211> LENGTH: 119
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 66
gggggcugga uacagagugg accggcuggc cccaucugga agacuucgag auacacuguu     60
gucuuacugc gcucaacagu guaucucgaa gucuuccaaa uggugccagc caucgcauu    119

<210> SEQ ID NO 67
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
ugacguauug ugaaauuugu uaa                                             23

<210> SEQ ID NO 68
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
aaacaaacau ggugcacuuc uu                                              22

<210> SEQ ID NO 69
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 69
aaggtggtac ctgaaaagaa gttgcccaug ttattttcgc tttatatgtg acgaaacaaa     60
catggtgcac ttcttttttcg gtatcatata gtga                                94

<210> SEQ ID NO 70
<211> LENGTH: 89
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 70
gggggugguu accugaaaaga aguugcccau guuauuuucg cuuuauaugu gacgaaacaa       60
acauggugca cuucuuuuuc gguaucauu                                         89

<210> SEQ ID NO 71
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
aaggtggtac ctgaatgacg tagtttgaaa ttacttacgc tttatatgtg acgtaacaaa       60
tttcacaata cgtcatttcg gtatcatata gtga                                   94

<210> SEQ ID NO 72
<211> LENGTH: 91
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
gggggugguu accugaaugac guauugugaa auuuguuaac gcuuuauaug ugacguuaac      60
aaauuucaca auacgucauu ucgguaucau u                                      91

<210> SEQ ID NO 73
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
auuaaugggu uuguguacu gua                                                23

<210> SEQ ID NO 74
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
uacaguacug ugauaacuga a                                                 21

<210> SEQ ID NO 75
<211> LENGTH: 75
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
ugcccuggcu caguuaucac agugcugaug cugucuauuc uaaagguaca guacugugau       60
```
aacugaagga uggca                                              75

<210> SEQ ID NO 76
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 76
ugcccuggat taatgggttt tgtgtactgt agucuauucu aaaggtacag tacacaaaac    60
ccattaatgg auggca                                                    76

<210> SEQ ID NO 77
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
aaggtgccct ggattaatgg gttttgtgta ctgtagtcta ttctaaaggt acagtacaca    60
aaacccatta atggatggca tatagtga                                       88

<210> SEQ ID NO 78
<211> LENGTH: 83
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78 ggggugccc uggauuaaug gguuuugugu acuguagucu auucuaaagg uacaguacac     60
aaaacccauu aauggauggc auu                                            83

<210> SEQ ID NO 79
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
uuccuuuccu gaucacuaug cau                                            23

<210> SEQ ID NO 80
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
uugcauaguc acaaaaguga uc                                             22

<210> SEQ ID NO 81

```
<211> LENGTH: 90
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
cucacagcug ccagugucau uuuugugauc ugcagcuagu auucucacuc caguugcaua      60
gucacaaaag ugaucauugg caggugüggc                                      90

<210> SEQ ID NO 82
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 82
cucacagcug ccaguuucct ttcctgatca ctatgcatcu aguauucuca cuccagatgc      60
atagtgatca ggaaaggaaa uuggcaggug uggc                                 94

<210> SEQ ID NO 83
<211> LENGTH: 106
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83
aaggctcaca gctgccagtt tcctttcctg atcactatgc atctagtatt ctcactccag      60
atgcatagtg atcaggaaag gaaattggca ggtgtggcta tagtga                    106

<210> SEQ ID NO 84
<211> LENGTH: 101
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 84
gggggcucac agcugccagu uuccuuuccu gaucacuaug caucuaguau ucucacucca      60
gaugcauagu gaucaggaaa ggaaauuggc aggugüggcu u                         101

<210> SEQ ID NO 85
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
cccuguucau uguaagcacu uuu                                             23

<210> SEQ ID NO 86
<211> LENGTH: 23
<212> TYPE: RNA
<213> ORGANISM: Artificial Sequence
```

<220> FEATURE:
<223> OTHER INFORMATION: Description of Artificial Sequence: Synthetic
oligonucleotide

<400> SEQUENCE: 86
aaaagugcuu acagugcagg uag                                            23

<210> SEQ ID NO 87
<211> LENGTH: 81
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 87
ccuuggccau guaaaagugc uuacagugca gguagcuuuu ugagaucuac ugcaauguaa    60
gcacuucuua cauuaccaug g                                              81

<210> SEQ ID NO 88
<211> LENGTH: 81
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 88
ccuuggccau guaaaagtgc ttacaatgaa cagggcuuuu ugagauccct gttcattgta    60
agcactttta cauuaccaug g                                              81

<210> SEQ ID NO 89
<211> LENGTH: 93
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 89
aaggccttgg ccatgtaaaa gtgcttacaa tgaacagggc tttttgagat ccctgttcat    60
tgtaagcact tttacattac catggtatag tga                                 93

<210> SEQ ID NO 90
<211> LENGTH: 88
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 90
gggggccuug gccauguaaa agugcuuaca augaacaggg cuuuugaga ucccuguuca    60 uuguaagcac uuuuacauua ccaugguu                                       88

<210> SEQ ID NO 91
<211> LENGTH: 90
<212> TYPE: RNA
<213> ORGANISM: Homo sapiens

<400> SEQUENCE: 91

```
cucacagcug ccagugucau uuuugugauc ugcagcuagu auucucacuc caguugcaua    60
gucacaaaag ugaucauugg caggugugge                                    90

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Arg Arg Arg Arg Arg Arg Arg Arg Arg
1               5

<210> SEQ ID NO 93
<211> LENGTH: 26
<212> TYPE: RNA
<213> ORGANISM: Mus sp.

<400> SEQUENCE: 93
aauuauguga gguagagacu augcac                                        26

<210> SEQ ID NO 94
<211> LENGTH: 87
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
agcgguggcc agugucauuu uugugauguu gcagcuagua auaugagccc aguugcauag    60
ucacaaaagu gaucauugga aacugug                                       87

<210> SEQ ID NO 95
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
taatacgact cactata                                                  17

<210> SEQ ID NO 96
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (3)..(30)
<223> OTHER INFORMATION: a, c, t, g, unknown or other
<220> FEATURE:
<221> NAME/KEY: modified_base
<222> LOCATION: (38)..(65)
<223> OTHER INFORMATION: a, c, t, g, unknown or other

<400> SEQUENCE: 96
aannnnnnnn nnnnnnnnnn nnnnnnnnnn tcatattnnn nnnnnnnnn nnnnnnnnn     60
```
nnnnntatag tga                                                         73

<210> SEQ ID NO 97
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (18)..(45)
<223> OTHER INFORMATION: a, c, t, g, unknown or other
<220> FEATURE:
<221> NAME/KEY: modified_base
<222> LOCATION: (53)..(80)
<223> OTHER INFORMATION: a, c, t, g, unknown or other

<400> SEQUENCE: 97
taatacgact cactatannn nnnnnnnnnn nnnnnnnnnn nnnnnaatat gannnnnnnn        60
nnnnnnnnnn nnnnnnnnnn tt                                                82

<210> SEQ ID NO 98
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (4)..(34)
<223> OTHER INFORMATION: a, c, t, g, unknown or other
<220> FEATURE:
<221> NAME/KEY: modified_base
<222> LOCATION: (42)..(72)
<223> OTHER INFORMATION: a, c, t, g, unknown or other

<400> SEQUENCE: 98
gggnnnnnnn nnnnnnnnnn nnnnnnnnnn nnnnaauaug annnnnnnnn nnnnnnnnnn        60
nnnnnnnnnn nnuu                                                         74

<210> SEQ ID NO 99
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (4)..(34)
<223> OTHER INFORMATION: a, c, t, g, unknown or other
<220> FEATURE:
<221> NAME/KEY: modified_base
<222> LOCATION: (42)..(72)
<223> OTHER INFORMATION: a, c, t, g, unknown or other

<400> SEQUENCE: 99
gggnnnnnnn nnnnnnnnnn nnnnnnnnnn nnnnaauaug annnnnnnnn nnnnnnnnnn        60
nnnnnnnnnn nnuu                                                      74

<210> SEQ ID NO 100
<211> LENGTH: 87
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
agcgguggcc agugucauuu uugugauguu gcagcuagua auaugagccc aguugcauag     60
ucacaaaagu gaucauugga aacugug                                        87

<210> SEQ ID NO 101
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (4)..(34)
<223> OTHER INFORMATION: a, c, t, g, unknown or other
<220> FEATURE:
<221> NAME/KEY: modified_base
<222> LOCATION: (42)..(47)
<223> OTHER INFORMATION: a, c, t, g, unknown or other
<220> FEATURE:
<221> NAME/KEY: modified_base
<222> LOCATION: (69)..(71)
<223> OTHER INFORMATION: a, c, t, g, unknown or other

<400> SEQUENCE: 101
gggnnnnnnn nnnnnnnnnn nnnnnnnnnn nnnaauaug annnnnnuug cauagucaca     60
aagugaucnn nuu                                                       73

<210> SEQ ID NO 102
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (4)..(34)
<223> OTHER INFORMATION: a, c, t, g, unknown or other
<220> FEATURE:
<221> NAME/KEY: modified_base
<222> LOCATION: (42)..(47)
<223> OTHER INFORMATION: a, c, t, g, unknown or other
<220> FEATURE:
<221> NAME/KEY: modified_base
<222> LOCATION: (71)..(73)
<223> OTHER INFORMATION: a, c, t, g, unknown or other

<400> SEQUENCE: 102
gggnnnnnnn nnnnnnnnnn nnnnnnnnnn nnnaauaug annnnnngug cauaguuuca     60
ugcucacaua nnnuu                                                     75

<210> SEQ ID NO 103

```
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (4)..(5)
<223> OTHER INFORMATION: a, c, t, g, unknown or other
<220> FEATURE:
<221> NAME/KEY: modified_base
<222> LOCATION: (28)..(33)
<223> OTHER INFORMATION: a, c, t, g, unknown or other
<220> FEATURE:
<221> NAME/KEY: modified_base
<222> LOCATION: (41)..(46)
<223> OTHER INFORMATION: a, c, t, g, unknown or other
<220> FEATURE:
<221> NAME/KEY: modified_base
<222> LOCATION: (70)..(72)
<223> OTHER INFORMATION: a, c, t, g, unknown or other

<400> SEQUENCE: 103
gggnnuugug agcaugaaac guugcacnnn nnnaauauga nnnnnngugc auaguuucau      60
gcucacaaan nnuu                                                       74

<210> SEQ ID NO 104
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (4)..(5)
<223> OTHER INFORMATION: a, c, t, g, unknown or other
<220> FEATURE:
<221> NAME/KEY: modified_base
<222> LOCATION: (29)..(34)
<223> OTHER INFORMATION: a, c, t, g, unknown or other
<220> FEATURE:
<221> NAME/KEY: modified_base
<222> LOCATION: (42)..(47)
<223> OTHER INFORMATION: a, c, t, g, unknown or other
<220> FEATURE:
<221> NAME/KEY: modified_base
<222> LOCATION: (71)..(73)
<223> OTHER INFORMATION: a, c, t, g, unknown or other

<400> SEQUENCE: 104
gggnnuaugu gagcaugaaa cuaugcacnn nnnnaauaug annnnnngug cauaguuuca      60
ugcucacaua nnnuu                                                      75

<210> SEQ ID NO 105
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
aaggtggtac ctgaatgacg tattgtgaaa tttgttaacg ctttatatgt gacgttaaca     60
```

```
<210> SEQ ID NO 106
<211> LENGTH: 89
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 106 gggggguggua ccugaaugac guaguuugaa auuacuuacg cuuuauaugu gacguaacaa        60
auuucacaau acgucauuuc gguaucauu                                          89

<210> SEQ ID NO 107
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
aaggtggtac ctgaatgacg tattgtgaaa tttgttaacg ctttatatgt gacgttaaca        60
aatttcacaa tacgtcattt cggtatcata tagtga                                  96

<210> SEQ ID NO 108
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (3)..(5)
<223> OTHER INFORMATION: a, c, t, g, unknown or other

<400> SEQUENCE: 108
aannntatag tga                                                           13
```